US006555523B1

(12) United States Patent
Prendergast

(10) Patent No.: US 6,555,523 B1
(45) Date of Patent: Apr. 29, 2003

(54) USE OF CIRSILIOL AND DERIVATIVES TO TREAT INFECTIONS

(76) Inventor: Patrick T. Prendergast, Baybrush, Straffan, County Kildare (IE)

(*) Notice: Subject to any disclaimer, the term of this patent is extended or adjusted under 35 U.S.C. 154(b) by 0 days.

(21) Appl. No.: 09/612,025

(22) Filed: Jul. 7, 2000

Related U.S. Application Data

(60) Provisional application No. 60/142,894, filed on Jul. 8, 1999, and provisional application No. 60/163,089, filed on Nov. 2, 1999.

(51) Int. Cl.$^7$ ................................................. A61K 31/70
(52) U.S. Cl. .......................................... 514/27; 514/456
(58) Field of Search ..................................... 514/27, 456

(56) References Cited

U.S. PATENT DOCUMENTS

| | | | |
|---|---|---|---|
| 3,450,717 A | | 6/1969 | Kramer et al. |
| 4,238,483 A | | 12/1980 | Frazier |
| 4,461,907 A | | 7/1984 | Batchelor et al. |
| 5,145,839 A | | 9/1992 | Beljanski |
| 5,489,585 A | | 2/1996 | Beuscher et al. |
| 5,510,375 A | | 4/1996 | Domagala et al. |
| 5,641,755 A | * | 6/1997 | Weichselbaum et al. ...... 514/44 |
| 5,650,432 A | | 7/1997 | Walker et al. |
| 6,063,809 A | | 5/2000 | Harris |

FOREIGN PATENT DOCUMENTS

| | | |
|---|---|---|
| EP | 0019081 A | 11/1980 |
| EP | 0348509 A | 1/1990 |
| EP | 0373986 A | 6/1990 |
| EP | 0861662 A | 9/1998 |
| JP | 02101013 A | 4/1990 |
| JP | 03007224 A | 1/1991 |
| JP | 04018019 A | 1/1992 |
| JP | 06199697 A | 7/1994 |
| JP | 07 002826 A | 1/1995 |
| JP | 07277969 A | 10/1995 |
| JP | 09 227373 A | 9/1997 |
| RO | 75776 A | 2/1983 |
| RO | 114410 | 4/1999 |
| WO | WO 92/06695 | 4/1992 |
| WO | WO 92/14458 A | 9/1992 |
| WO | WO 97/47270 A | 12/1997 |
| WO | WO 98/42188 A | 10/1998 |
| WO | WO 98/46238 A | 10/1998 |
| WO | WO 99/44578 A | 9/1999 |
| WO | WO 99/49862 A | 10/1999 |
| WO | WO 00/32177 A | 6/2000 |
| WO | WO 00/32201 A | 6/2000 |

OTHER PUBLICATIONS

Kusumoto, Hattori, Miyaichi, Tomimori, Hanaoka, Namba; effects of Flavonoids and Alkaloids on Reverse Transcriptase, Apr. 8, 1991, pp. 14.*

Vrijsen, et al., "The poliovirus–induced shut–off of cellular protein synthesis persists in the presence of 3–methylquercetin, a flavonoid which blocks viral protein and RNA synthesis", Antiviral Research, 7 35–42 (1987).

Brinkworth, et al., "Flavones are Inhibitors of HIV–1 Proteinase", Biochemical and Biophysical Research Communications, vol. 188, No. 2, 631–637 (1992).

Wang, et al., "Antitumor Agents. 166. Synthesis and Biological Evaluation of 5,6,7, 8–Substituted–2–phenylthiochromen–4–ones", J. Med. Chem. 39, 1975–1980 (1996).

Nagai, et al., "Mode of action of the anti–influenza virus activity of plant flavonoids, 5,7, 4'–trihydroxy–8–methoxyflavone, from the roots of Scutellaria baicalensis", Antiviral Research 26, 11–25 (1995).

Kaul, et al., "Antiviral Effect of Flavonoids on Human Viruses", Journal of Medical Virology 15:71–79 (1985).

Castrillo, et al., "3–Methylquercetin Is a Potent and Selective Inhibitor of Poliovirus RNA Synthesis", Virology 152, 219–227 (1986).

Horie, et al., "Syntheses of 5,6,7– and 5,7,8–Trioxygenated 3',4'–Dihydroxyflavones Having Alkoxy Groups and Their Inhibitory Activities against Arachidonate 5–Lipoxygenase", J. Med. Chem. 29, 2256–2262 (1986).

So, et al., "Inhibition of Human Breast Cancer Cell Proliferation and Delay of Mammary Tumorigenesis by Flavonoids and Citrus Juices", Nutrition and Cancer, vol. 26, No. 2, 168–180 (1996).

Guthrie, et al., "Inhibition of Mammary Cancer by Citrus Flavonoids", Flavonoids in the Living System, 227–236 (1998).

So, et al., "Inhibitor of proliferation of estrogen receptor–positive MCF–7 human breast cancer cells by flavonoids in the presence and absence of excess estrogen", Cancer Letters 112 127–133 (1997).

Glinski, Z., et al., "The Antimicrobial Activity of Propolis", Med. Weter. vol. 43, No. 2, pp 74–79 (1987).

Lee, Ji–hyun, et al., "Antiherpetic activities of natural naringenin alone and in combinations with acyclovir and vidarabine", Yakhak Hoeji, vol. 43, No. 1, pp. 77–84 (1999).

Lee, Ji–Hyun, et al., "Antiviral activity of some flavonoids on herpes simplex viruses", Saengyak Hakhoechi, vol. 30(1), pp. 34–39 (1999).

(List continued on next page.)

Primary Examiner—Kenneth R. Horlick
(74) Attorney, Agent, or Firm—Heather L. Callahan

(57) ABSTRACT

The invention provides the use of flavin compounds such as cirsiliol, 3',4'-diacetoxy-5,6,7-trimethoxyflavone or naringin in the treatment of infections, particularly for viral (e.g., HCV, HIV, a picornavirus genus virus or a respiratory virus) or parasite (e.g., toxoplasmosis) infections. Also provided are compositions for use in the methods.

22 Claims, No Drawings

OTHER PUBLICATIONS

Critchfield, J.W., et al., "Inhibition of HIV Activation in Latently Infected Cells by Flavonoid Compounds", *Aids Research Human Retroviruses*, vol. 12, p. 39–46 (1996).

Pathak, D., et al., "Flavanoids as Medicinal Agents—Recent Advances", *Fitoterapia*, vol. 62, No. 5, pp. 371–389 (1991).

Liu, K.C.S.C., et al., "Antimalarial Activity of *Artemisia Annua* Flavonoids from Whole Plants and Cell Cultures", *Plant Cell Rep.*, vol. 11, No. 12, pp. 637–640 (1992).

Hu, Chang Qi, et al., "Anti–aids agents, 10. Acacetin–7–0–beta–D–galactopyranoside, an anti–HIV principle from Chrysanthemum morifolium and a structure–activity correlation with some related flavonoids", *N. Nat. Prod.*, vol. 57(1), pp. 42–51 (1994).

Khalid, S.A., et al., "Potential antimalarial candidates from African Plants: An in vitro approach using *Plasmodium falciparum*", *J. Ethnopharmacol.* vol. 15(2), pp. 201–209 (1986).

Kaij, A. Kamb M. et al., "Search for New Antiviral Agents of Plant Origin", *Pharm. Acta Helv.*, vol. 67, No. 5–6, pp. 130–147 (1992).

Wleklik, M., et al., "Structural basis for antiviral activity of flavonoids—naturally occurring compounds", *Acta Virol.* (Engl. Ed.), vol. 32(6), pp. 522–525 (1988).

Tsuchiya, Yoshinori, et al., "Antiviral activity of natural occurring flavonoids in vitro", *Chem. Pharm. Bull.*, vol. 33(9), pp. 3881–3886 (1985).

Kusumoto, I.T., et al., "A comparative study on the inhibitory effects of flavonoids and alkaloids on reverse transcriptases of different retroviruses", *Shoyakugaku Zasshi*, vol. 47(3), pp. 291–294 (1993).

Kusumoto, Ines Tomco, et al., "Effects of flavonoids and alkaloids on reverse transcriptase", *Shoyakugaku Zasshi*, vol. 45(3), pp. 240–254 (1991).

Wacker, Von A., et al., "Antiviral activity of plant components. Part 1. Flavonoids." *Arzneim.–Forsch*, vol. 28, No. 3, pp. 347–350 (1978) [In German].

Lin, Yuh–Meei, et al., "In Vitro Anti–HIV Activity of Biflavanoids Isolated from *Rhus succedanea* and *Garcinia multiflora*", *J. Nat. Prod.*, vol. 60(9), pp. 884–888 (1997).

Grael, C.F.F., et al., "Trypanocidal activity of crude extracts and compounds from *Lychnophora granmongolense (Duarte) semir* and *leitao filho (vernonieae, asteraceae)*", *Boll. Chim. Farm.* vol. 138, No. 2, LVII, (1999).

Schinor, E.C., et al., "Biological activity of the crude extracts and some isolated substances from *Moquinia kiingi* (DC) H. Robinson", *Boll. Chim. Farm.* vol. 138, No. 2, LXXIII (1999).

Lopes, N.P., et al., "Flavonoids and lignans from *Virola surinasmensis* twigs and their in vitro activity against *Trypanosoma cruzi*", *Planta Med.*, vol. 64, No. 7, pp. 667–669 (1998).

Mahmood, N., et al., "Inhibition of HIV Infection by Flavanoids", *Antiviral Res.*, vol. 22, No. 2–3, pp. 189–199 (1993).

Kaul, T.N., et al., "Interaction of flavonoids and viruses in–vitro potential role in anti viral therapy", *J. Allergy Clin. Immunol.*, vol. 69 (1 part 2), pp. 104 (1982).

Burnham, Weldon S., et al., "Synthesis and antiviral activity of 4'–hydroxy–5,6,7,8–tetramethoxyflavone", *J. Med. Chem.*, vol. 15(10), pp. 1075–1076 (1972).

Raz, B., et al., "Phytochemical investigation of the African medicinal plant *Ehretia amoena* for the identification of trypanocidal molecules", *Trop. Med. Int. Health*, vol. 1, No. 6, pp. A30–A31 (1996).

Zani, C.L., et al., "Trypanocidal components of *Pluchea quitoc L.*", *Phytotherapy Research*, vol. 8/6, pp. 375–377 (1994).

Gonzalez, J., et al., "In vitro activity of natural products against the trypamastigote form of *trypanosoma cruzi*", *Phytother. Res.*, vol. 4(1), pp. 1–4, (1990).

Lien, Eric J., et al., "Epstein–Barr virus DNA polymerase inhibitors from Chineses herbs: use of preliminary screening, psycicochemical properties and taxonomy for new lead compounds generation", *Chin. Pharm. J.*, vol. 50(4), pp. 344–247 (1998).

Ribeiro, A., et al., "Trypanocidal flavonoids from *Trixis vauthieri*", *Journal of Natural Products*, vol. 60(8), pp. 836–841 (1997).

Formica, J.V., et al., "Review of the Biology of Quercetin and Related Bioflavonoids", *Food and Chemical Toxicology*, vol. 33, No. 12, pp. 1061–1080 (1995).

Fesen, M.R., et al., "Inhibition of HIV–1 integrase by flavones, caffeic acid phenethyl ester (cape) and related compounds", *Biochemical Pharmacology*, vol. 48, No. 3, pp. 595–608 (1994).

Alves, C.N., et al., "A quantum chemical and statistical study of flavonoids compounds with anti–HIV activity", *Theochem*, vol. 491, pp. 123–131 (1999).

Vlietinck, A.J., et al., "Plant–derived leading compounds for chemotherapy of human immunodeficiency virus (HIV) infection", *Planta Medica*, vol. 64, No. 2, pp. 97–109 (1998).

Ono, et al., "Differential inhibitory effects of various flavonoids on the activities of reverse transcriptase and cellular DNA and RNA polymerases", *Eur. J. Biochem.*, vol. 190, No. 3, pp. 469–476 (1990) [Abstract].

Egan, D., et al., "The Pharmacology, Metabolism, Analysis and Applications of Coumarin and Coumarin–Related Compounds", *Drug Metab. Rev.*, vol. 22, No. 5, pp. 503–529 (1990).

\* cited by examiner

USE OF CIRSILIOL AND DERIVATIVES TO TREAT INFECTIONS

CROSS-REFERENCE TO RELATED APPLICATIONS

This application claims priority of U.S. provisional application Ser. No. 60/142,894, filed Jul. 8, 1999, now abandoned and U.S. provisional application Ser. No. 60/163,089, filed Nov. 2, 1999, both of which are incorporated herein by reference.

BACKGROUND OF THE INVENTION

The present invention is directed to the use of flavones, flavanones and related compounds, to treat infectious conditions such as viral or parasite infections.

The common cold and other respiratory infections are often associated with or caused by infection by a number of viruses that can infect the respiratory system ("respiratory viruses"), such as rhinoviruses, paramyxoviruses such as respiratory syncytial virus (RSV), enteroviruses and coronaviruses. Methods to treat such infections are usually limited to treating symptoms and not the infectious agent.

RSV is a virus classified in the genus Pneumovirus of the Paramyxovirus family. This virus can cause lower respiratory tract infections such as bronchiolitis or pneumonia in, e.g., infants, young children, elderly persons or immunosuppressed patients. RSV can progress to cause serious or fatal symptoms in some cases (see e.g., Englund et al., *Ann. Int. Med.* 1988 1:203). Ribavirin aerosol has been used to treat RSV infections, but its toxicity limits its systemic use (se e.g., Gladu et al., *J. Toxic Env. Health* 1989 28:1). A vaccine of inactivated RSV has been developed, but significant side effects are associated with it and additional therapies are needed.

Otitis media, middle ear inflammation, is another common early childhood infection. Agents responsible for otitis media typically are respiratory syncytial viruses, rhinoviruses, influenza A viruses or adenoviruses (Henderson et al., *New Eng. J. Med.* 1982 1377; Ruuskanin et al., *Pedr. Infect. Dis. J.* 1989 94). Prevention of respiratory virus infections decreases the incidence of otitis media (Heikkinen et al., *AJDC* 1991 445). Agents that treat or prevent such infections are needed.

Influenza viruses are members of the Orthomyxovirus family. Seasonal outbreaks occur almost yearly and occasional worldwide pandemics also arise. Treatment with vaccines are usually effective at preventing the disease, but the vaccine is needed each year, due to the variation of the flu viruses that arise each year. Amantadine has been used for treatment of ongoing infection, but it has some CNS toxicity. Influenza virus infection can progress to a primary influenza viral pneumonia, which can not be treated with amantadine or rimantidine. Additional agents to treat or prevent such infections are needed.

Herpesviruses such as herpes simplex viruses and related viruses (e.g., HSV-1, HSV-2, EBV, CMV, HHV-6, HHV-8) are members of the Herpesviridae family. Transmission of the viruses can arise from direct contact, e.g., HSV-1 through the oral cavity and HSV-2 through the genital tract. A number of therapeutic agents are available, e.g., acyclovir, trifluridine and vidarabine. These agents are not uniformly effective to treat the spectrum of infections that are associated with these viruses and additional agents to treat these infections are needed.

Retroviruses are associated with a number of infections, notably AIDS, and some cancers. The human immunodeficiency virus, HIV, (HIV-1, HIV-2, HTLV-III, LAV) is believed to be responsible for causing immune deficiency conditions in humans. Related viruses can lead to similar conditions in animals, e.g., SIV or SHIV in primates or FIV in cats. Loss of cell-mediated immunity and development of eventually fatal opportunistic infections frequently occurs in HIV infections. Most available treatment options have one or more limitations, such as toxicities or unwanted side effects and complicated dosing regimens. Large-scale efforts to identify additional treatment options for retrovirus infections are underway.

Hepatitis viruses such as human hepatitis A virus ("HAV"), human hepatitis B virus ("HBV"), and human hepatitis C virus ("HCV"), can lead to significant symptoms and mortality. For example, HCV infection is common, with estimates of worldwide prevalence of chronic hepatitis ranging from 90 million up to over 200 million. There is no vaccine or candidate vaccine for pre-exposure prophylaxis and no effective globulin for post-exposure prophylaxis. Related viruses of the Togaviridae, Hepadnaviridae, Flaviviridae and Picornaviridae families, including alphaviruses (also known as arboviruses, group A), flaviviruses (also known as arboviruses, group B)(such as yellow fever, as well as hepatitis C and hepatitis G), Rubiviruses (also known as rubella viruses)(such as rubella) and pestiviruses (also known as mucosal disease viruses, such as bovine virus diarrhea virus (BVDV)) are also significant causes of disease and mortality. Therapies for some of these infections exist, e.g., interferon treatment for HCV infection, but the treatments are not always effective and can have serious unwanted side effects. Considerable efforts are underway to identify additional therapeutic agents to use in treating these infections.

The protozoan parasite *Toxoplasma gondii* is the etiologic agent of toxoplasmosis. The organism is a sporozoan that lives as an intracellular parasite in macrophages. It has evolved mechanisms to avoid killing by host cell defenses such as oxygen radicals and lysosomal enzymes. The parasite synthesizes molecules that appear to prevent lysosomes in infected macrophages from fusing with phagosomes that contain the parasite.

A number of flavonoids, coumarins and related compounds, methods to obtain them and their uses have been described. See, e.g., J. A. Manthey and B. S. Buslig, editors, *Flavonoids in the living system, Advances in experimental medicine and biology*, volume 439, Plenum Press, New York, 1998, chapter 15 (pages 191–225), chapter 16 (pages 227–235) and chapter 17 (pages 237–247), C. N. Alves et al., *Theochem.* 1999 491:123–131, J-H. Lee et al., *Saengyak Hakhoechi* 1999, 30:34–39, S. J. Semple et al., *J. Ethnopharmacology* 1999 68:283–288, E. Z. Baum et al., *Biochemistry* 1996 35:5847–5855, J. W. Critchfield et al., *AIDS Res. Hum. Retroviruses* 1996 12:39–46, H. K. Wang et al., *J. Med. Chem.* 1996 39:1975–1980, T. Nagai et al., *Antiviral Res.* 1995 26:11–25, T. Nagai et al., *Biol. Pharm. Bull.* 1995 18:295–299, N. Mahmood et al., *Antiviral Res.* 1993 22:189–99, J. A. Beutler et al., *J. Nat. Prod.* 1992 55:207–213, R. I. Brinkworth et al., *Biochem. Biophys. Res. Commun.* 1992 188:631–637, M. S. Chapman et al., *J. Mol. Biol.* 1991 217:455–463, I. T. Kusumoto et al., *Shoyakugaku Zassi* 1991 45:240–54, T. Konoshima et al., *Shoyakugaku Zassi* 1989 42:135–141, R. Vrijsen et al., *Antiviral Res.* 1987 7:35–42, J. L Castrillo et al., *Virology* 1986 152:219–227, T. Horie et al., *J. Med. Chem.* 1986 29:2256–2262, T. N. Kaul et al., *J. Med. Virol.* 1985 15:71–79, T. Yoshinori et al., *Chem. Pharm. Bull.* 1985 33:3881–3886, P. G. Higgins et al., *British. Soc. Antimicrobial Chemother* 1984 403–409, Y.

Graziani et al., *Eur. J. Biochem.* 1983 135:583–589 and U.S. Pat. Nos. 6,063,809, 5,955,256, 5,877,208, 5,869,701, 5,830,894, 5,510,375, 5,489,585 and 4,238,483.

The present invention provides compounds for use in these infectious conditions to treat or prevent them, or to ameliorate one or more symptoms associated with such infections. Also provided are compounds and compositions suitable for use in the methods.

SUMMARY OF THE INVENTION

In accordance with the present invention, a method is provided to treat or prevent a virus or a parasite infection comprising administering to a subject having the virus or parasite infection an effective amount of a compound having the formula 1 or 2

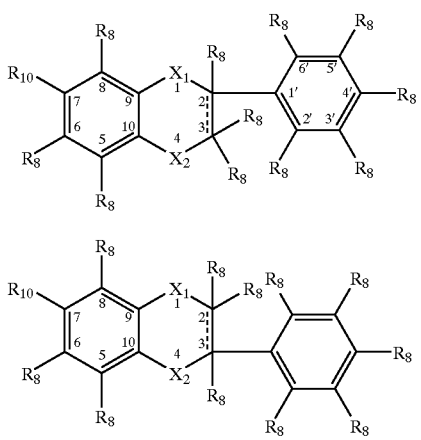

wherein a double or a single bond is present at the dotted line and, when a double bond is present, (i) the optionally substituted phenyl ring at the 2- or 3-position is present and the $R_8$ that is bonded to that position is absent, and (ii) one $R_8$ at the adjacent 2- or 3-position is absent;

$X_1$ is —O— or —C($R_8$)$_2$—;

$X_2$ is —C(O)— or —C($R_{11}$)$_2$—;

each $R_8$ independently is —H, —OH, —SH, halogen, $C_{1-6}$ alkly, $C_{1-6}$ alkoxy, glucuronide, a moiety that can hydrolyze to hydroxyl, a protecting group, a $C_{1-25}$ fatty acid, the residue of a formula 1 or 2 compound where a hydrogen atom is removed to form the formula 1 or 2 compound radical, —CH$_2$CH=C(CH$_3$)$_2$, glucoside, a group having structure (B) or (C),

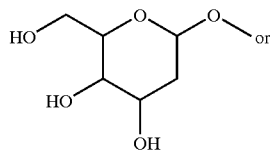

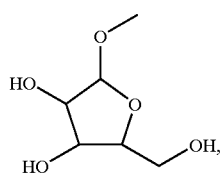

or, either $R^8$ and $R^{10}$ at the 7 and 8 positions or both $R^8$ at the 5 and 6 positions together comprise a 6-membered aromatic ring and the remaining $R^8$ are independently selected from the substituents defined above, or two $R^8$ bonded to the same carbon atom are oxygen (=O) or sulfur (=S);

$R_{10}$ is hydroxyl (—OH), thiol (—SH), $C_{1-6}$ alkyl, $C_{1-6}$ alkoxy, a protecting group, a moiety that can hydrolyze to hydroxyl or thiol, neohesperidoside, apioglucoside, rutinoside, glucoside, galactoside, rhamnoside, arabinoside, or a stereoisomer, hydrate, analog, derivative or metabolite of any of these moieties, any of which are optionally independently substituted at one or more hydrogen atoms with —OH, halogen, $C_{1-6}$ alkyl, $C_{1-6}$ alkoxy, glucuronide or a $C_{1-25}$ fatty acid or $R_{10}$ is —H, —OH or halogen;

each $R_{11}$ independently is —H, —OH, —SH, halogen, $C_{1-6}$ alkyl, $C_{1-6}$ alkoxy, phenyl, glucuronide, a $C_{1-25}$ fatty acid, or both $R_{11}$ together are =O or =S; and the salts, stereoisomers, positional isomers, metabolites, tautomers, ionized forms and solvates thereof.

In some embodiments, the infection is a viral infection such as a picornavirus, a human immunodeficiency virus ("HIV") or human hepatitis C virus ("HCV") virus infection. In other embodiments, the infection is a parasite infection such as toxoplasmosis or malaria.

DETAILED DESCRIPTION OF THE INVENTION

As used herein and unless otherwise stated or implied by context, the following terms have the meanings defined here.

A "patient" or "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents.

"Alkyl" as used herein, unless stated to the contrary, is a saturated or unsaturated $C_1$–$C_{18}$ hydrocarbon containing 1, 2, 3, 4, 5, 6, 7, 8, 9, 10, 11, 12, 13, 14, 15, 16, 17 or 18 carbon atoms in the form of normal, secondary, tertiary, cyclic or mixed structures. Examples are —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH$_2$CH$_2$CH$_3$, —CH(CH$_3$)CH$_2$CH$_2$CH$_3$, —CH(CH$_2$CH$_3$)$_2$, —C(CH$_3$)$_2$CH$_2$CH$_3$, —CH(CH$_3$)CH(CH$_3$)$_2$, —CH$_2$CH$_2$CH(CH$_3$)$_2$, —CH$_2$CH(CH$_3$)CH$_2$CH$_3$, —CH$_2$C(CH$_3$)$_3$, —CH$_2$CH$_2$CH$_2$CH$_2$CH$_2$CH$_3$, —CH(CH$_3$)CH$_2$CH$_2$CH$_2$CH$_3$, —CH(CH$_2$CH$_3$)(CH$_2$CH$_2$CH$_3$), —C(CH$_3$)$_2$CH$_2$CH$_2$CH$_3$, —CH(CH$_3$)CH(CH$_3$)CH$_2$CH$_3$, —CH(CH$_3$)CH$_2$CH(CH$_3$)$_2$, —C(CH$_3$)(CH$_2$CH$_3$)$_2$, —CH(CH$_2$CH$_3$)CH(CH$_3$)$_2$, —C(CH$_3$)$_2$CH(CH$_3$)$_2$, —CH(CH$_3$)C(CH$_3$)$_3$, cyclopropyl, cyclobutyl, cyclopropylmethyl, cyclopentyl, cyclobutylmethyl, 1-cyclopropyl-1-ethyl, 2-cyclopropyl-1-ethyl, cyclohexyl, cyclopentylmethyl, 1-cyclobutyl-1-ethyl, 2-cyclobutyl-1-ethyl, 1-cyclopropyl-1-propyl, 2-cyclopropyl-1-propyl, 3-cyclopropyl-1-propyl, 2-cyclopropyl-2-propyl, 1-cyclopropyl-2-propyl, —CH=CH$_2$, —CH=CHCH$_3$, —CH$_2$CH=CH$_2$, —C(=CH$_2$)(CH$_3$), —CH=CHCH$_2$CH$_3$, —CH$_2$CH=CHCH$_3$, —CH$_2$CH$_2$CH=CH$_2$, —CH=C (CH$_3$)$_2$, —CH$_2$C(=CH$_2$)(CH$_3$), —C(=CH$_2$)CH$_2$CH$_3$, —C(CH$_3$)=CHCH$_3$, —CH(CH$_3$)CH=CH$_2$, —C=CHCH$_2$CH$_2$CH$_3$, —CHCH=CHCH$_2$CH$_3$, —CHCH$_2$CH=CHCH$_3$, —CHCH$_2$CH$_2$CH=CH$_2$, —C(=CH$_2$)CH$_2$CH$_2$CH$_3$, —C(CH$_3$)=CH$_2$CH$_2$CH$_3$, —CH(CH$_3$)CH=CHCH$_3$, —CH(CH$_3$)CH$_2$CH=CH$_2$, —CH$_2$CH=C(CH$_3$)$_2$, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, —CCH, —CCCH$_3$, —CH$_2$CCH, —CCCH$_2$CH$_3$, —CH$_2$CCCH$_3$, —CH$_2$CH$_2$CCH, —CH(CH$_3$)CCH, —CCCH$_2$CH$_2$CH$_3$, —CH$_2$CCCH$_2$CH$_3$, —CH$_2$CH$_2$CCCH$_3$ and —CH$_2$CH$_2$CH$_2$CCH.

"Halogen" or "halo" means fluorine (—F), chlorine (—Cl), bromine (—Br) or iodine (—I) and if more than one halogen is referred to (e.g., two or more variable groups may be a halogen), each halogen is independently selected.

"PEG" means an ethylene glycol polymer that contains about 20 to about 2000000 linked monomers, typically about 50–1000 linked monomers, usually about 100–300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

Terms such as "excipient", "carrier", "pharmaceutically acceptable carrier" or the like are used interchangeably herein and they all mean a component or an ingredient that is acceptable in the sense of being compatible with the other ingredients of compositions or formulations as disclosed herein and not overly deleterious to the patient or animal to which the formulation is to be administered. As used here, excipients and carriers include solids and liquids. Typical excipients include cellulose, methylcellulose, starch, microcrystalline cellulose, lactose, sucrose, glucose, magnesium stearate, a C$_{2-12}$ alcohol (e.g., ethanol), glycerol, peanut oil, a PEG, propylene glycol or a vegetable oil such as safflower oil, sesame oil or soybean oil. Such components are typically used in the pharmaceutical or veterinary formulation arts, e.g., fillers, binders, disintegrants and lubricants.

Unless otherwise specified, expressions that refer to "a formula 1 or 2 compound(s)", and the like mean compositions or methods, e.g., methods to treat a viral or parasite infection as disclosed herein, where one or more than one formula 1 or formula 2 compound is present, typically 1, 2, 3 or 4. The formula 1 and 2 compounds are sometimes collectively referred herein to as the "compounds of the invention", or "compounds of the present invention" or the like.

Terms such as a "moiety that can convert to hydroxyl or thiol in vivo", "a derivative that can convert to a formula 1 or 2 compound" and similar terms means an organic moiety that can convert chemically or enzymatically to a hydroxyl or thiol group or to the formula 1 or 2 compound in vitro or in vivo. Typically these moieties comprise an ester structure (—C(O)—O—) that links the formula 1 or 2 compound to the organic moiety and the conversion is chemical or enzymatic hydrolysis, e.g., hydrolysis is mediated by low pH in the gut or esterase activity in cells (e.g., virus infected cells), tissues, blood or plasma.

"Ester" or "ester structure" means a moiety that comprises a —C(O)—O— structure. Typically, esters as used here comprise an organic moiety containing about 1–50 carbon atoms (e.g., about 2–12 carbon atoms) and 0 to about 10 independently selected heteroatoms (e.g., O, S, N, P, Si), where the organic moiety is bonded to a formula 1 steroid nucleus at R$^2$ through the —C(O)—O— structure, e.g., organic moiety-C(O)—O-steroid or organic moiety-O—C(O)-steroid. The organic moiety usually comprises one or more of any of the organic groups described above, e.g., C$_{1-20}$ alkyl moieties, C$_{2-20}$ alkenyl moieties, C$_{2-20}$ alkynyl moieties, aryl moieties, C$_{2-9}$ heterocycles or substituted derivatives of any of these, e.g., comprising 1, 2, 3, 4 or more substituents, where each substituent is independently chosen. Typical substitutions for hydrogen or carbon atoms in these organic groups include 1, 2, 3, 4 or more, usually 1, 2, or 3 —O—, —S—, —NR$^{PR}$— (including —NH—), —C(O)—, =O, =S, —N(R$^{PR}$)$_2$ (including —NH$_2$), —C(O)OR$^{PR}$ (including —C(O)OH), —OC(O)R$^{PR}$ (including —O—C(O)—H), —OR$^{PR}$ (including —OH), —SR$^{PR}$ (including —SH), —NO$_2$, —CN, —NHC(O)—, —C(O)NH—, —OC(O)—, —C(O)O—, —O—A8, —S—A8, —C(O)—A8, —OC(O)—A8, —C(O)O—A8, =N—, —N=, =N—OH, —OPO$_3$(R$^{PR}$)$_2$, —OSO$_3$H$_2$ or halogen moieties or atoms, where each R$^{PR}$ is —H, an independently selected protecting group or both R$^{PR}$ together comprise a protecting group, and A8 is C$_{1-8}$ alkyl, C$_{2-8}$ alkenyl, C$_{2-8}$ alkynyl, C$_{1-4}$ alkyl-aryl (e.g., benzyl), aryl (e.g. phenyl) or C$_{0-4}$ alkyl-C$_{2-9}$ heterocycle. Substitutions are independently chosen. The organic moiety includes compounds defined by the R$_4$ variable. The organic moieties exclude obviously unstable moieties, e.g., —O—O—, except where such unstable moieties are transient species that one can use to make a compound with sufficient chemical stability for the one or more of the uses described herein. The substitutions listed above are typically substituents that one can use to replace one or more carbon atoms, e.g., —O— or —C(O)—, or one or more hydrogen atom, e.g., halogen, —NH$_2$ or —OH.

As used herein, the neohesperidoside, rutinoside and glucoside groups have the structures

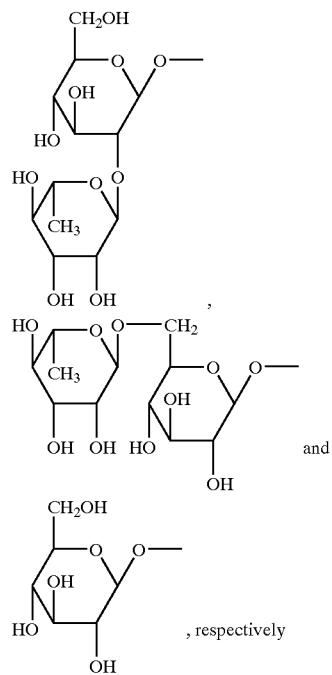

, respectively wherein one or more of the hydrogen atoms are optionally independently substituted with hydroxy, halogen, C$_{1-6}$ alkyl, C$_{1-6}$ alkoxy, glucuronide, a C$_{1-10}$ ester, or a C$_{1-25}$ fatty acid, e.g., acetate, acetyl or butyrate.

Heterocycle. "Heterocycle" or "heterocyclic" includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5566; and U.S. Pat. No. 5,763,483, all of which are incorporated herein by reference.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or $C_{1-6}$ alkyl, usually —H. Examples are as described for heterocycle.

Protecting groups. Various groups that the formula 1, 1 or 2 compounds may comprise include, e.g., substituted alkyl groups, substituted alkenyl groups, esters or substituted heterocycles, which can contain one or more reactive moieties such as hydroxyl, or thiol. Intermediates used to make formula 1 or formula 1 or 2 compounds may be protected as is apparent in the art. Noncyclic and cyclic protecting groups and corresponding cleavage reactions are described in "Protective Groups in Organic Chemistry", Theodora W. Greene (John Wiley & Sons, Inc., New York, 1991, ISBN 0-471-62301-6) (hereafter "Greene"). In the context of the present invention, these protecting groups are groups that can be removed from the molecule of the invention without irreversibly changing the covalent bond structure or oxidation/reduction state of the remainder of the molecule. For example, the protecting group, —X, that is bonded to a —OX or —NHX group can be removed to form —OH or —NH$_2$, respectively, without affecting other covalent bonds in the molecule. At times, when desired, more than one protecting group can be removed at a time, or they can be removed sequentially. In compounds of the invention containing more than one protecting group, the protecting groups are the same or different.

Protecting groups are intended to be removed by known procedures, although it will be understood that the protected intermediates fall within the scope of this invention. The removal of the protecting group may be arduous or straightforward, depending upon the economics and nature of the conversions involved. In general, one will use a protecting group with exocyclic amines or with carboxyl groups during synthesis of a formula 1 compound. For most therapeutic applications amine groups should be deprotected. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the invention compounds. Suitable protecting groups and criteria for their selection are described in T. W. Greene and P. G. M. Wuts, Eds. "Protective Groups in Organic Synthesis" 2nd edition, Wiley Press, at pp. 10–142, 143–174, 175–223, 224–276, 277–308, 309–405 and 406–454, which is incorporated herein by reference.

Determination of whether a group is a protecting group is made in the conventional manner, e.g., as illustrated by Kocienski, Philip J.; *"Protecting Groups"* (Georg Thieme Verlag Stuttgart, New York, 1994) (hereafter "Kocienski"), Section 1.1, page 2, and Greene Chapter 1, pages 1–9; and U.S. Pat. No. 5,763,483, all of which are incorporated herein by reference. In particular, a group is a protecting group if when, based on mole ratio, 90% of that protecting group has been removed by a deprotection reaction, no more than 50%, preferably 25%, more preferably 10%, of the deprotected product molecules of the invention have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment of the invention, a group is a protecting group if when, based on mole ratio determined by conventional techniques, 90% of that protecting group has been removed by a conventional deprotection reaction, no more than 50%, preferably 25%, more preferably 10%, of the deprotected product molecules of the invention have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected molecule of the invention.

Protecting groups are also described in detail together with general concepts and specific strategies for their use in Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1–20, Chapter 2, Hydroxyl Protecting Groups, pages 21–94, Chapter 3, Diol Protecting Groups, pages 95–117, Chapter 4, Carboxyl Protecting Groups, pages 118–154, Chapter 5, Carbonyl Protecting Groups, pages 155–184, Chapter 6, Amino Protecting Groups, pages 185–243, Chapter 7, Epilog, pages 244–252, and Index, pages 253–260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxyl protecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "Reagents and Solvents" at page xv are each incorporated in their entirety herein.

Typical hydroxy protecting groups are described in Greene at pages 14–118 and include Ethers (Methyl); Substituted Methyl Ethers (Methoxymethyl, Methylthiomethyl, t-Butylthiomethyl, (Phenyidimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, alpha-Naphthyldiphenylmethyl, p-methoxyphenyidiphenylmethyl, Di(p-methoxyphenyl)phenylmethyl, Tri(p-methoxyphenyl)methyl, 4-(4'-Bromophenacyloxy)phenyidiphenylmethyl, 4,4', 4"-Tris(4,5-dichlorophthalimidophenyl)methyl, 4,4', 4"-Tris(levulinoyloxyphenyl)methyl, 4,4', 4"-Tris(benzoyloxyphenyl)methyl, 3-(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl, S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Triphenylmethylsilyl, t-Butylmethoxyphenylsilyl); Esters (Formate, Benzoylformate, cetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3-tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N', N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically hydroxy protecting groups include subtituted methyl ethers, substituted benzyl ethers, silyl ethers, and esters including sulfonic acid esters, still more typically, trialkylsilyl ethers, tosylates and acetates.

Typical 1,2- and 1,3-diol protecting groups are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, alpha-Methoxybenzylidene, 1-(N,N-Dimethylamino)ethylidene Derivative, alpha-(N,N-Dimethylamino)benzylidene Derivative, 2-Oxacyclopentylidene); and Silyl Derivatives (Di-t-butylsilylene Group, 1,3-(1,1,3,3-Tetraisopropyldisiloxanylidene) Derivative, Tetra-t-butoxydisiloxane-1,3-diylidene Derivative, Cyclic Carbonates, Cyclic Boronates, Ethyl Boronate, Phenyl Boronate).

More typically, 1,2- and 1,3-diol protecting groups include epoxides and acetonides.

Stereoisomers. The formula 1 or 2 compounds include enriched or resolved optical isomers at any or all asymmetric atoms as are apparent from the depictions. Both racemic and diasteromeric mixtures, as well as the individual optical isomers can be isolated or synthesized so as to be substantially free of their enantiomeric or diastereomeric partners, and these are all within the scope of the invention. Chiral centers may be found in invention compounds at, for example, $R^8$, or $R^{10}$.

One or more of the following methods are used to prepare the enantiomerically enriched or pure isomers herein. The methods are listed in approximately their order of preference, i.e.; one ordinarily should employ stereospecific synthesis from chiral precursors before chromatographic resolution before spontaneous crystallization.

Stereospecific synthesis is described in the examples. Methods of this type conveniently are used when the appropriate chiral starting material is available and reaction steps are chosen that do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis.

If a suitable stereospecific synthesis cannot be empirically designed or determined with routine experimentation then those skilled in the art would turn to other methods. One method of general utility is chromatographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—Intentional Symposium on Chiral Separations, Sep. 3–4, 1987, which is incorporated herein by reference. Examples of chiral columns that could be used to screen for the optimal separation technique would include Diacel Chriacel OD, Regis Pirkle Covalent D-phenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separating the conjugates by ordinary column chromatography. This is a very suitable method, particularly when the embodiment contains a free hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group.

Enzymatic resolution is another method of potential value. In such methods one prepares covalent derivatives of the enantiomers in the racemic mixture, generally lower alkyl esters, and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enantiomeric mixture separates from solution or a melt as a conglomerate, i.e., a mixture of enantiomerically pure crystals, then the crystals can be mechanically separated, thereby producing the enantiomerically enriched preparation. This method, however, is not practical for large-scale preparations and is of limited value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4): Part 2, Resolution of Enantiomer Mixture, pages 217–435; more particularly, section 4, Resolution by Direct Crystallization, pages 217–251, section 5, Formation and Separation of Diastereomers, pages 251–369, section 6, Crystallization-Induced Asymmetric Transformations, pages 369–378, and section 7, Experimental Aspects and Art of Resolutions, pages 378–435; still more particularly, section 5.1.4, Resolution of Alcohols, Transformation of Alcohols into Salt-Forming Derivatives, pages 263–266, section 5.2.3, Covalent Derivatives of Alcohols, Thiols, and Phenols, pages 332–335, section 5.1.1, Resolution of Acids, pages 257–259, section 5.1.2, Resolution of Bases, pages 259–260, section 5.1.3, Resolution of Amino Acids, page 261–263, section 5.2.1, Covalent Derivatives of Acids, page 329, section 5.2.2, Covalent derivatives of Amines, pages 330–331, section 5.2.4, Covalent Derivatives of Aldehydes, Ketones, and Sulfoxides, pages 335–339, and section 5.2.7, Chromatographic Behavior of Covalent Diastereomers, pages 348–354, all of which are incorporated herein by reference.

In some embodiments, the ester is an organic moiety comprising 1, 2, 3, 4, 5, 6, 7, 8, 9 10, 11 or 12 carbon atoms and 0, 1, 2, 3, 4, 5, 6, 7 or 8 independently selected O, S, N, P, or Si atoms, but, if a Si or P atom is present, only one Si or P is present, wherein the organic moiety is optionally selected from $C_{1-12}$ alkyl, $C_{2-12}$ alkenyl, $C_{2-12}$ alkynyl, aryl, a $C_{2-9}$ heterocycle or a substituted derivative of any of these comprising 1, 2, 3, 4 or more substituents, wherein each substituent is independently chosen and is selected from —O—, —S—, —NR$^{PR}$— (including —NH—), —C(O)—, =O, =S, —N(R$^{PR}$)$_2$ (including —NH$_2$), —C(O)OR$^{PR}$ (including —C(O)OH), —OC(O)R$^{PR}$ (including —O—C(O)—H), —OR$^{PR}$ (including —OH), —SR$^{PR}$ (including —SH), —NO$_2$, —CN, —NHC(O)—, —C(O)NH—, —OC(O)—, —C(O)O—, —O—A8, —S—A8, —C(O)—A8, —OC(O)—A8, —C(O)O—A8, =N—, —N=, =N—OH, —OPO$_3$(R$^{PR}$)$_2$, —OSO$_3$H$_2$ and halogen moieties or atoms, where each R$^{PR}$ is —H, an independently selected protecting group or both R$^{PR}$ together comprise a protecting group, and A8 is C$_{1-8}$ alkyl, C$_{2-8}$ alkenyl, C$_{2-8}$ alkynyl, C$_{1-4}$ alkyl-aryl (e.g., benzyl), aryl (e.g. phenyl) or C$_{1-4}$ alkyl-C$_{2-9}$ heterocycle. G12 moieties include —CH$_3$, —C$_2$H$_5$, —C$_3$H$_7$, —C$_4$H$_9$, —C$_6$H$_{13}$, —CH$_2$—C$_6$H$_5$, —C$_2$H$_4$—C$_6$H$_5$, —C$_3$H$_6$—C$_6$H$_5$, —C$_6$H$_5$, —CH$_2$-heterocycle, —CH$_2$—CH$_2$-heterocycle and a heterocycle, and of which are substituted with one, two, three or more independently selected —O—, —S—, —F, —Cl, —Br, —I, —NH—, =O, —CN, —OCH$_3$, —OC$_2$H$_5$, —OC$_4$H$_9$, —NO$_2$, —NH$_2$, —COOH, or —NH—C(O)— moieties.

An aspect of the invention comprises administering an effective amount of a compound of formula 1 or 2 compound preventing or treating one or more conditions described herein, e.g., Trypanosome or Plasmodium infections in a subject. Exemplary formula 1 or 2 compounds include bavachinin A, didymin (isosakuranetin-7-rutinoside or neoponcirin), flavanomarein (isookanine-7-glucoside), flavanone azine, flavanone diacetylhydrazone, flavanone hydrazone, silybin, which has the structure

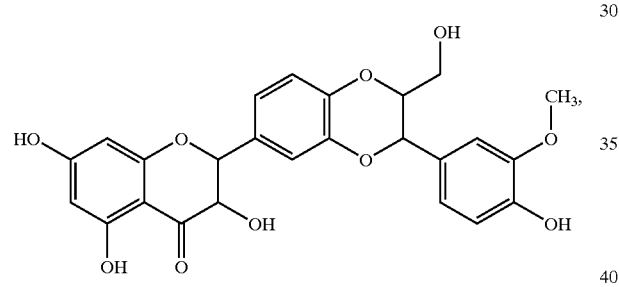

silychristin,

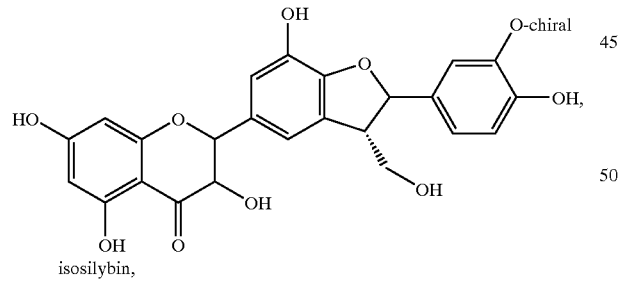

isosilybin,

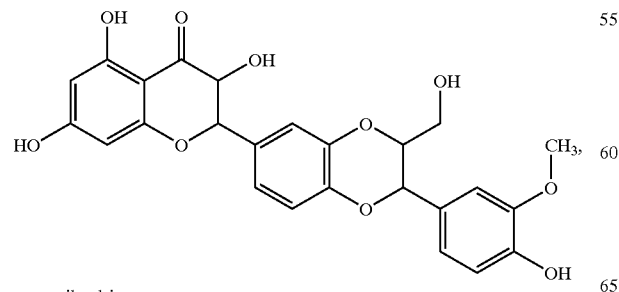

silandrin,

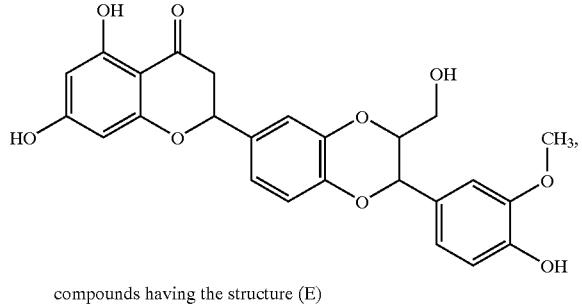

compounds having the structure (E)

(E)

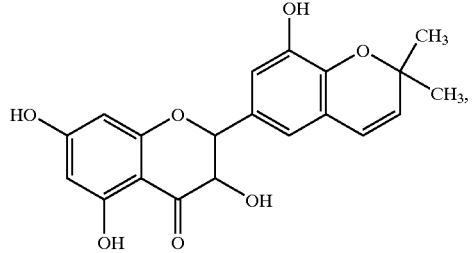

baicalein trimethyl ether (4'-hydroxy-5,6,7-trimethoxyflavone)

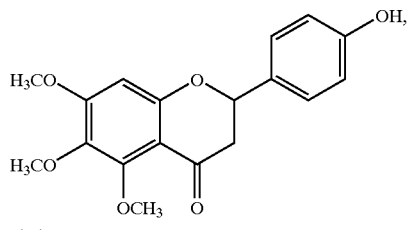

3',4'-dihydroxy-α-napthoflavone,

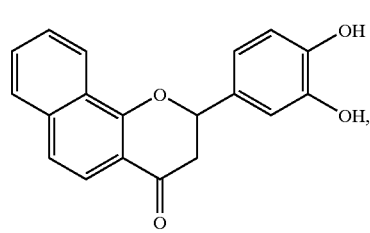

3',4'-dihydroxy-β-napthoflavone,

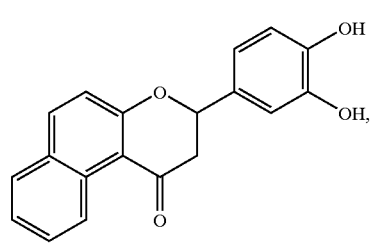

3',4'-dibenzyloxy-5,6,7-trimethoxyflavone,

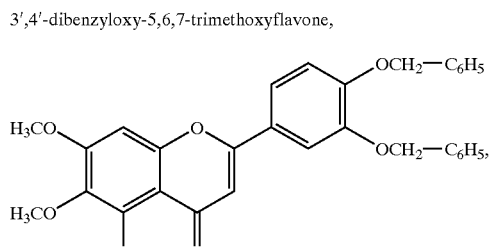

3',4'-dihydroxy-5,6,7-trimethoxyflavone,

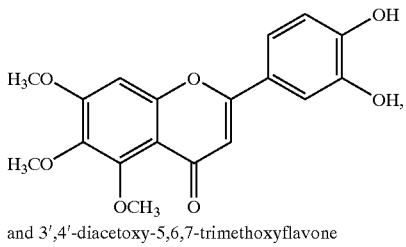

and 3',4'-diacetoxy-5,6,7-trimethoxyflavone

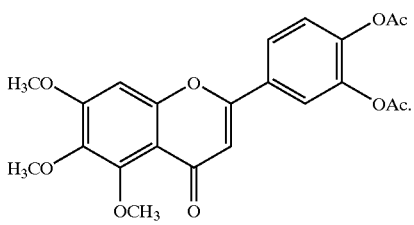

Also within the scope of the invention are compounds related to compounds of formula 1 or 2 wherein one of the bonds between atoms 1, 2, 3 and 4 is absent; that is the ring comprising atoms 1, 2, 3 and 4 is not closed, for example 2-(3,4-dibenzyloxy)-4,5,6-trimethoxyacetophenone

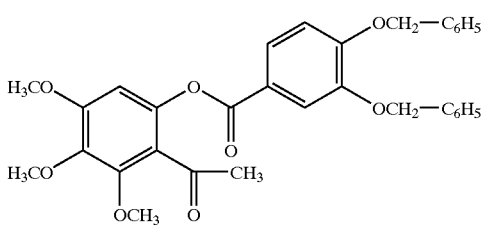

and 3',4'-dibenzyloxy-2-hydroxy-4,5,6-trimethoxydibenzoylmethane

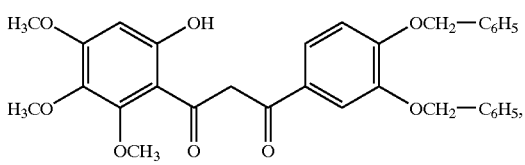

The formula 1 and 2 compounds encompass a number of natural and synthetic flavonoids, including certain flavones, flavans, and their iso analogs. Such compounds include compounds of formulas 50–65

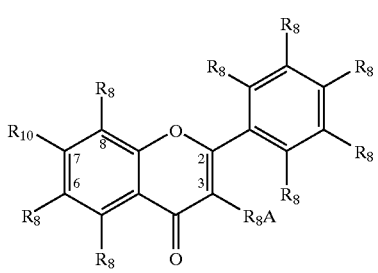

50

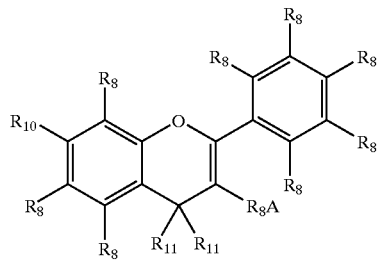

51

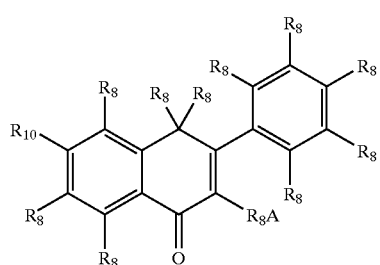

52

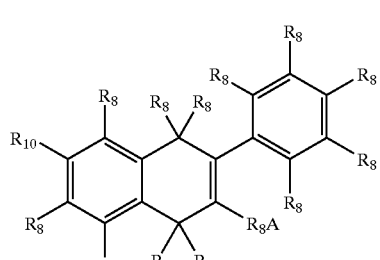

53

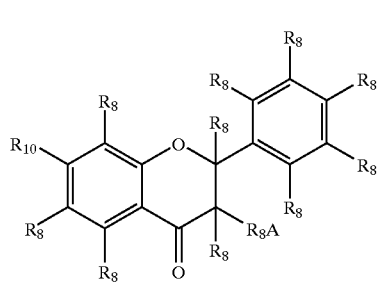

54

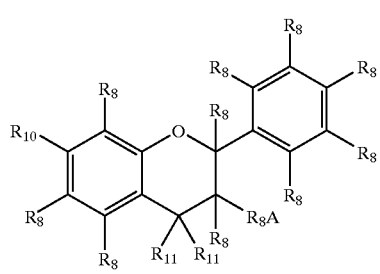

55

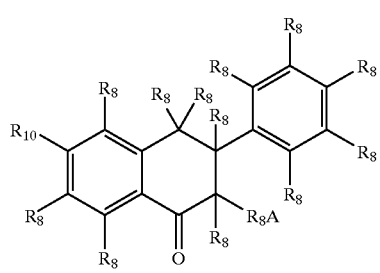

56

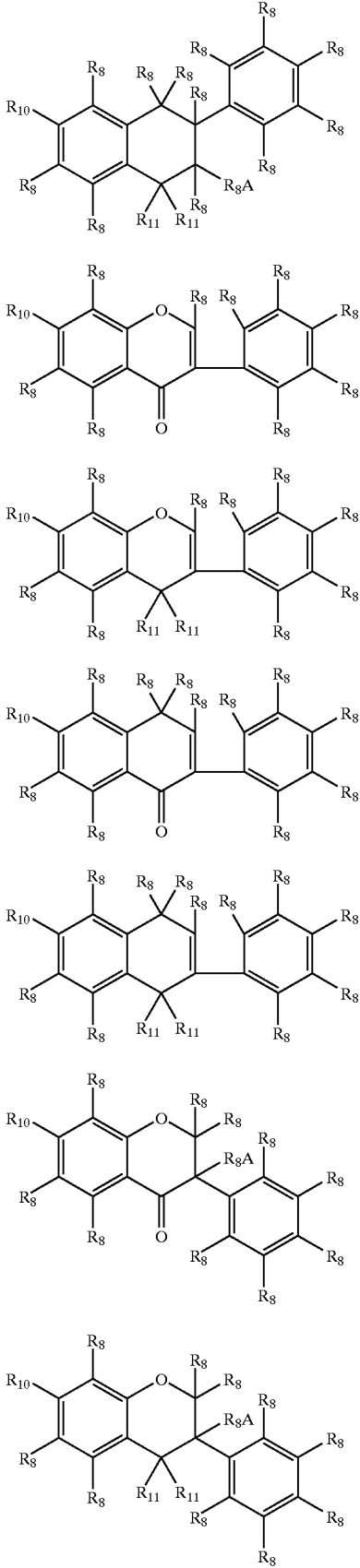

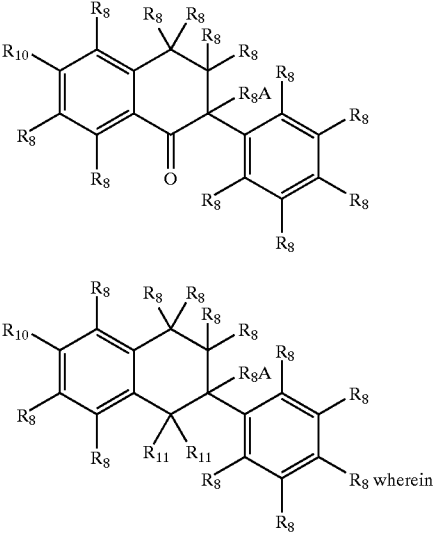

wherein
$R_8$ at the 6-position independently are —H, —OH, —F, —Cl, —Br, —I, $C_{1-6}$ alkyl, $C_{1-6}$ alkoxy, glucuronide, a $C_{1-25}$ fatty acid, glucoside, —$CH_2CH$=$C(CH_3)_2$ or a group having the structure (B);

$R_8$ at the 8-position independently are —H, —OH, —F, —Cl, —Br, —I, $C_{1-6}$ alkyl, $C_{1-6}$ alkoxy, glucuronide, a $C_{1-25}$ fatty acid, glucoside, —$CH_2CH$=$C(CH_3)_2$ or the residue of a formula 50–65 compound where a hydrogen atom is removed to form the formula 50–65 radical;

$R_8A$ independently are —H, —OH, —F, —Cl, —Br, —I, $C_{1-6}$ alkyl, $C_{1-6}$ alkoxy, glucuronide, a $C_{1-25}$ fatty acid, glucoside, —$CH_2CH$=$C(CH_3)_2$ or a group having the structure (C);

the remaining $R_8$ independently are —H, —OH, —F, —Cl, —Br, —I, $C_{1-6}$ alkyl, $C_{1-6}$ alkoxy, glucuronide, a $C_{1-25}$ fatty acid or —$CH_2$—$CH$=$C(CH_3)_2$; and $R_{10}$ (i) is —OH or —F, —Cl, —Br, —I, $C_{1-6}$ alkyl, $C_{1-6}$ alkoxy, neohesperidoside, apioglucoside, rutinoside, glucoside, galactoside, rhamnoside, arabinoside, or a stereoisomer, hydrate, analog, derivative or metabolite of any of these moieties, any of which are optionally independently substituted at one or more hydrogen atoms with —OH, —F, —Cl, —Br, —I, $C_{1-6}$ alkyl, $C_{1-6}$ alkoxy, glucuronide or a $C_{1-25}$ fatty acid, or (ii) $R_{10}$ is the radical of bavachinin A, didymin, flavanomarein, flavanone azine, flavanone diacetylhydrazone, flavanone hydrazone, silybin, silychristin, isosilybin, silandrin, a moiety of structure (E) or a stereoisomer or metabolite of any of these moieties.

Invention embodiments include the use of any of the compounds of formula 50–65 in the therapeutic applications in this disclosure, wherein 1, 2, 3, 4, 5 or 6 of the $R_8$, $R_{10}$ or $R_{11}$ moieties are independently selected from optionally substituted $C_{1-10}$ alkoxy, an optionally substituted $C_{1-10}$ ester or an optionally substituted saccharide or oligosaccharide, e.g., 1, 2, 3, 4, 5, 6 or 7, $R_8$, $R_{10}$ and $R_{11}$ independently are —$OCH_3$, —$OC_2H_5$, —$OC_4H_9$, —$OC_6H_{13}$, —$OCOOH$, —$OCH_2COOH$, —$OCH_2CH_2CH_2COOH$, —$OC_5H_{10}COOH$, —$OCH_2CH_2OCH_3$, —$OCH_2CH_2SCH_3$, —$OC(O)CH_3$, —$OC(O)C_2H_5$, —$OC(O)C_4H_9$, —$OC(O)C_6H_{13}$, —$OC(O)$ $CH_2CH_2OCH_3$, $-OC(O)CH_2CH_2SCH_3$, $-OC(O)-CH_2-C_6H_5$, $-OC(O)-CH_2-C_6H_4OCH_3$, $-OC(O)-CH_2-C_6H_4OH$, $-OC(O)-CH_2-C_6H_4OC(O)OH$, $-OH$, $-SH$, $=O$, $=S$, phenyl, benzyl, glucoside, rhamnoside, riboside, 2'-deoxyriboside or arabinoside. Typically in these embodiments, none, one, two or three of the $R_8$, $R_{10}$ and/or $R_{11}$ moieties independently comprise $-SH$ or $=S$.

Generally, the formula 1 or 2 compounds comprise 0, 1, 2 or 3 $=O$ moieties, which includes any of the compounds of structure 50–65 and any of the embodiments described herein.

For embodiments where two variable moieties, e.g., two $R_8$ at the 2 or 3 position or two $R_{11}$ or at $X_2$, are bonded to the same carbon atom of a formula 1 or 2 compound, (1) one of the two variable groups may be hydrogen while the other is hydrogen or one of the other defined substituents for that variable group or (2) both variable groups together are oxygen ($=O$) or sulfur ($=S$).

Methods of administration and formulations. Compounds of the family of compounds outlined herein have been found in to have valuable pharmaceutical properties as, e.g., antiviral agents, in relation to the viruses, which were heretofore unknown.

Compounds used according to this invention are administered as treatments against infections by any suitable route including enteral, parenteral, topical, oral, rectal, nasal or vaginal routes. Parenteral routes include subcutaneous, intramuscular, intravenous and sublingual administration. Topical routes include buccal and sublingual administration. Additionally, compositions of the present invention may be implanted into a patient or injected using a drug delivery system. See, for example, Urquhart, et al., Ann. Rev. Pharmacol. Toxicol. 24: 199–236 (1984); Lewis, ed. "Controlled Release of Pesticides and Pharmaceuticals" (Plenum Press, New York, 1981); U.S. Pat. No. 3,773,919; and U.S. Pat. No. 3,270,960.

The present invention further provides use of any compound described herein in the manufacture or preparation of formulations, and especially pharmaceutical formulations, for use in treatments against specific infectious agents such as HIV or respiratory viruses. The invention also provides the pharmaceutical formulations themselves. Such formulations typically comprise one or more acceptable excipients and a formula 1 or 2 compound.

Pharmaceutical preparations prepared according to the invention include the compounds described herein contained in a gelatin capsule, in tablet form, dragee, syrup, suspension, topical cream, suppository, injectable solution, or kits for the preparation of syrups, suspension, topical cream, suppository or injectable solution just prior to use. Also, compounds described herein may be included in composites, which facilitate its slow release into the blood stream, e.g., silicon disc, polymer beads.

Pharmaceutical preparations prepared according to the invention include the employment of compounds described herein in admixture with conventional excipients, that is, pharmaceutically acceptable organic or inorganic carrier substances which do not deleteriously react with the compounds. Suitable pharmaceutically acceptable carriers include, but are not limited to water, salt solutions, alcohols, gum arabic, vegetable oils, gelatin, carbohydrates, magnesium stearate, talc, silicic acid, viscous paraffin, fatty acid mono- and di-glycerides, etc.

The formulations may conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17$^{th}$ edition, Nema et al., *PDA J. Pharm. Sci. Tech.* 1997 51:166–171. Methods to make invention formulations include the step of bringing into association or contacting a formula 1 or 2 compound with one or more excipients or carriers. In general, the formulations are prepared by uniformly and intimately bringing into association the formula 1 or 2 compound with liquid excipients or finely divided solid excipients or both, and then, if appropriate, shaping the product.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

Examples of an injectable form include solutions, suspensions and emulsions. The compounds of the present invention can be injected in association with a pharmaceutical carrier such as normal saline, Ringer's solution, dextrose solution and other aqueous carriers known in the art. Appropriate non-aqueous carriers may also be used and examples include fixed oils and ethyl oleate. A suitable carrier is 5% dextrose in saline. Frequently, it is desirable to include additives in the carrier such as buffers and preservatives or other substances to enhance isotonicity and chemical stability.

To achieve satisfactory bioavailability using formula 1 or 2 compounds, the compounds are frequently administered in the form of a hot liquid (preferably as hot as possible, such as at least 65–70° C.), e.g., dissolved in hot water. Solubility is typically enhanced at such higher temperatures, i.e., solubility at 70° C. can be about 10 times higher than solubility at 40° C. Alternatively or additionally, bioavailability can be improved by administering the compounds according to the present invention within liposomes, the manufacture of such liposomes and the insertion of active ingredients into such liposomes being well known in the art.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators and the like. Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The dosage of any one or more of the compounds described herein which is effective in treatment against respiratory virus infections, e.g., rhinovirus or influenza infections, will depend on factors including the specific compound or combination of compounds being utilized, the mode of administration, and the organism being treated. Dosages of a particular compound or combinations of compound, each belonging to the compounds described herein, for a given host can be determined using conventional considerations; for example, by customary comparison of the differential activities of the subject compounds and of a known agent, that is, by means of an appropriate pharmacological protocol. With respect to the duration of treatment, it is typical for skilled clinicians to monitor patients in order to determine when the treatment is providing therapeutic benefit, and to determine whether to increase dosage, decrease dosage, discontinue therapy, resume therapy or alter therapy.

Further, the effectiveness of a particular regimen can be monitored by following over time the presences of viral particles in blood samples of an organism being treated. There are available commercially kits for the detection of viral antigens. It will be possible to cause a reduction, over a period of about two months, in the level of detectable p24 antigen in the blood serum of a patient by means of administration of compounds described herein. A better measure of the progression of the level of infection would be the percentage infected macrophage population. Monocytes/macrophage cells obtained from either the blood or the lung during a course of treatment with compounds described herein will show a reduction in recoverable HIV antigen as the therapy progresses.

In one embodiment of the invention, a pharmaceutical formulation comprising any of cirsiliol, tangeretin, gossypetin, 7,8-Benzoflavone, 6-Hydroxyflavone, flavone, naringin, hesperetin, 3(4'-bromophenyl) coumarin is administered at the rate of 1 unit dose to 10 unit doses per day, and preferably1 unit dose to 4 unit doses per day. The doses are given for periods of up to twelve weeks and in certain cases may be given for the life of the patient or depending on the patient's medical requirements at less frequent intervals.

In one embodiment of the invention, a pharmaceutical formulation comprising a compound as described herein is in combination with other anti-viral agents.

In one aspect of the invention, a unit dose comprises about 0.01 to about 5000 mg of a formula 1 or 2 compound, typically about 5–1000 mg, often about 10–500 mg, e.g., for most human applications, one will administer about 3 g/day of naringin in one or more unit or subunit dosages.

In one embodiment of the invention, the pharmaceutical formulation is administered orally in unit doses once per day when the compound is in a slow release form or in 1, 2, 3, 4, 5, 6, 7 or 8 unit doses or sub doses per day when the compound is in its native form. The pharmaceutical formulation may be administered intravenously in unit doses comprising a compound from those described herein in the range of about 0.1 mg to about 80 mg per Kg of body weight, typically about 0.5–25 mg/kg/day.

In one embodiment of the invention, a pharmaceutical formulation comprising a compound from those as described herein is administered using an emulsifying or semi-emulsifying formulation to improve absorption from the small intestine. Such an emulsion may be formulated using a derivative of coconut oil e.g. Miglyol 812.

In another embodiment of the invention, the method includes the step of treating a patient with an immune system booster both prior to and/or simultaneously while a pharmaceutical formulation comprising a compound from those described herein is being administered.

The present invention is also directed to pharmaceutical formulations that contain one or more of the compounds according to the present invention together with ribavirin, alpha interferon, or both ribavirin and alpha interferon.

In some embodiments, the formula 1 or 2 compound that is present in the compositions or that is used in the methods disclosed herein is completely dissolved in aqueous or non-aqueous excipients. However, in some embodiments, e.g., transient compositions or some formulations, the formula 1 or 2 compound is partially dissolved or mixed while the remaining portion is present as a solid, which can be a suspension or a colloid. In related embodiments, the formula 1 or 2 compound is incompletely dissolved and is present as a suspension or gel.

In addition to compounds of formula 1 or 2, or their salts, the pharmaceutical compositions may contain other additives, such as pH adjusting additives, in particular, agents such as acids, bases, or buffers, including sodium lactate, sodium acetate, and sodium gluconate. Further, such compositions may contain microbial preservatives, such as methylparaben, propylparaben, benzyl alcohol and benzyl benzoate. If a multiple use vial is supplied, the pharmaceutical composition should likewise include such a microbial preservative. The formulations may be, of course, lyophilized, using techniques well known in the art.

Formulations of the present invention suitable for oral administration may be presented as discrete units such as capsules, cachets or tablets each containing a predetermined amount of the formula 1 or 2 compound; as a powder or granules; as solution or a suspension in an aqueous liquid or a non-aqueous liquid; or as an oil-in-water liquid emulsion or a water-in-oil liquid emulsion. The formula 1 or 2 compound may also be presented as a bolus, electuary or paste.

A tablet may be made by compression or molding, optionally with one or more excipients. Compressed tablets may be prepared by compressing in a suitable machine the formula 1 or 2 compound in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the formula 1 or 2 compound therein.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make up the emulsifying wax, and the wax together with the oil and fat make up the emulsifying ointment base, which forms the oily dispersed phase of the cream formulations. Emulgents and emulsion stabilizers suitable for use in formulations comprising a formula 1 or 2 compound include Tween® 60, Span® 80, cetostearyl alcohol, benzyl alcohol, myristyl alcohol, glyceryl mono-stearate and sodium lauryl sulfate.

Formulations suitable for buccal administration include lozenges comprising a formula 1 or 2 compound in a flavored basis, usually sucrose and acacia or tragacanth; pastilles comprising the formula 1 or 2 compound in an inert basis such as gelatin and glycerin, or sucrose and acacia.

Formulations for rectal administration may be presented as a suppository with a suitable base comprising for example cocoa butter or a salicylate.

Formulations suitable for intrapulmonary or nasal administration will have a particle size for example in the range of 0.01 to 200 microns (including particle sizes in a range between 0.01 and 500 microns in increments of 0.1 microns such as 0.1, 0.2, 0.3, 0.4, 0.5, 1, 2, 5, 30 microns, 35 microns, etc.), which is administered by inhalation through the nasal passage or by inhalation through the mouth so as to reach the various bronchi or alveolar sacs. Formulations suitable for aerosol or dry powder administration may be prepared according to conventional methods and may be delivered with other therapeutic agents such as compounds heretofore used in the treatment or prophylaxis of Trypanosome infections. Metered dose inhalers readily administer inhalation therapy.

Formulations suitable for vaginal administration may be presented as pessaries, tampons, creams, gels, pastes, foams or spray formulations containing in addition to the formula 1 or 2 compound such carriers or excipients as are known in the art to be appropriate.

Formulations suitable for parenteral administration are sterile and include aqueous and non-aqueous injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Unit dosage formulations will typically contain a daily dose or unit daily sub-dose, as recited above, or an appropriate fraction thereof, of a formula 1 or 2 compound.

To the extent not already indicated, it will be understood by those of ordinary skill in the art that any one of the various specific embodiments herein described and illustrated may be further modified to incorporate features shown in any of the other embodiments disclosed herein.

The invention provides veterinary compositions comprising at least one formula 1 or 2 compound together with a veterinary carrier. Also, the formula 1 or 2 compound may be present in the animal's feed or water. Excipients for veterinary applications may include compounds, e.g., small amounts of chloroform, that may not be generally suitable for human use. Many of the formula 1 or 2 compounds are soluble in organic solvents, e.g., many of the coumarins are soluble in chloroform, acetone or DMF.

Veterinary carriers are materials useful for the purpose of administering the composition to cats, dogs, horses, mice, rats, hamsters, rabbits and other animals and may be solid, liquid or gaseous materials that are otherwise inert or acceptable in the veterinary art and are compatible with the formula 1 or 2 compound. These veterinary compositions may be administered orally, parenterally or by any other desired route, e.g., as described herein.

Applications. The compositions and formulations disclosed herein are useful in the treatment of, or ameliorate one or more symptoms associated with, the conditions or infections disclosed herein. These compositions and formulations may also be used to treat, or ameliorate one or more symptoms associated with or caused by, a retroviral infection such as a HIV1 or HIV2 infection in humans. As used herein, phrases such as "amelioration of one or more symptoms associated with" means that such compounds or formulations may be used to reduce replication of an infectious agent or to reduce the number of infectious agents that are present in a subject or to ameliorate one or more symptoms associated with, or caused by, the condition or infection (e.g., reduced fever, a shortened duration of, or reduced level of, pain, or a noticeable reduction of or elimination of diarrhea, fatigue or involuntary weight loss (e.g., weight loss of more than about 4–5% of body weight over a relatively short time period).

Exemplary viral infections that are included in the invention for treatment, prophylaxis or amelioration of one or more symptoms using an effective amount of a formula 1 or 2 compound include Central European encephalitis virus, Chikungunya virus, Congo-Crimean hemorrhagic fever virus, Dengue viruses 1–4, Eastern equine encephalitis virus, Echoviruses 1–9 and 11–27 and 29–34, Enteroviruses 68–71, Epstein-Barr virus (human herpesvirus 4), Hantaan virus, human Hepatitis A virus, human Hepatitis B virus, human Hepatitis C virus, human herpes simplex viruses 1 and 2, human enteric coronavirus, human cytomegalovirus (human herpesvirus 5), human herpesviruses 6A, 6B, and 7, human immunodeficiency viruses 1 and 2, human respiratory coronaviruses 229E and $OC_{43}$, human T-lymphotropic viruses 1 and 2, HTLV/BLV viruses, influenza viruses A and B, Japanese encephalitis virus, Kyasanur forest virus, La Crosse virus, Lassa virus, Mayaro virus, Measles virus, Mumps virus, Murray Valley encephalitis virus, Norwalk and related viruses, O'nyong-nyong virus, Omsk hemorrhagic fever virus, Oropouche virus, Papillomaviruses 1–60, Parainfluenza viruses 1, 2, 3 or 4, Parvoviruses, Parvovirus B-19, Polioviruses 1, 2 or 3, RA-1 virus, Picornavirus genus viruses, Rabies virus, Respiratory syncytial virus, Rhinoviruses 1–113, Rift Valley fever virus, Rocio virus, Ross River virus, Rubella virus, Russian spring-summer encephalitis virus, Sandfly fever-Naples virus, Sandfly fever-Sicilian virus, St. Louis encephalitis virus, SV 40 virus, Tahyna virus, Vaccinia virus, Varicella-zoster virus (human herpesvirus 3), Variola virus, Venezuelan equine encephalitis virus, Vesicular stomatitis viruses, West Nile virus, Eastern equine encephalitis virus, Yellow fever virus, Avian reticuloendotheliosis virus, Avian sarcoma and leukosis viruses, B virus (Cercopithecus herpesvirus), Berne virus (horses), Border disease virus (sheep), Bovine enteroviruses 1–7, Bovine ephemeral fever virus, Bovine immunodeficiency virus, Bovine leukemia virus, Bovine mamillitis virus, Bovine papillomaviruses, Bovine papular stomatitis virus, Bovine respiratory syncytial virus, Bovine virus diarrhea virus, Breda virus (calves), Canine adenovirus 2, Canine distemper virus, Canine parvovirus, Caprine arthritis-encephalitis virus, Eastern equine encephalitis virus, Encephalomyocarditis virus, Equine abortion virus, Equine adenoviruses, Equine coital exanthema virus, Equine infectious anemia virus, Equine rhinopneumonitis virus (EHV4), Feline immunodeficiency virus, Feline infectious peritonitis virus, Feline panleukopenia virus, Feline sarcoma and leukemia viruses, Foot-and-mouth disease viruses, Hemagglutinating encephalomyelitis virus (swine), Hog cholera virus, Infectious bovine rhinotracheitis virus, Infectious bronchitis virus (fowl), Infectious canine hepatitis virus, Infectious hematopoietic necrosis virus (fish), Infectious laryngotracheitis virus (fowl), Influenza viruses of swine, horses, seals, and fowl, Japanese encephalitis virus, Maedilvisna virus (sheep), Marek's disease virus (fowl), Mink enteritis virus, Minute virus of mice, Mouse hepatitis viruses, Mouse mammary tumor virus, Mouse poliomyelitis virus (Theiler's virus), Mucosal disease virus (cattle), Newcastle disease virus (fowl), Parainfluenza virus 3, Parainfluenza virus 1 (Sendai virus), Peste-des-petits-ruminants virus (sheep and goats), Pneumonia virus of mice, Progressive pneumonia virus of sheep, Pseudorabies virus, Rabies virus, Rift Valley fever virus, Rinderpest virus, Rotaviruses, Shope papillomavirus, Simian immunodeficiency viruses (SIV, SHIV), Swine vesicular disease virus, Tick-borne encephalitis viruses, Transmissible gastroenteritis virus (swine), Turkey bluecomb virus, Venezuelan equine encephalitis virus, Vesicular stomatitis viruses, Wesselsbron virus and Western equine encephalitis virus. The compounds disclosed herein, e.g., as named in numbered embodiment 35 or in any of the claims, can be used for any of these infections or conditions.

Compounds of formula 1 or 2, including ones that are new compounds per se, are useful for treating or preventing bacterial, mycoplasma, fungal or yeast infections, e.g., gram positive or gram negative bacteria infections, or for ameliorating one or more symptoms associated with such infections. Exemplary infections include ones caused by isolates, species, strains or variants of the Bartonella, Bordetella, enterotoxigenic, enteropathogenic, enteroinvasive or *enterohemorrhagic Escherichia*, Haemophilus, Helicobacter, Mycobacterium, Listeria, Neisseria, Pseudomonas, Salmonella, Shigella, Staphylococcus, Streptococcus, Vibrio, Yersinia, Aspergillus, Candida or *Cryptococcus taxonomic* groups. Such infections may occur concomitantly with a viral or parasite infection, e.g., as described herein, or they may be not be accompanied by any apparent or diagnosed viral or parasite infection.

All references cited herein are incorporated herein by reference in their entirety.

Enumerated embodiments. Aspects of the invention include the following enumerated embodiments, which further illustrate the invention and aspects thereof or related subject matter. In general, any of the compounds disclosed herein is suitable for use in any of the clinical conditions or infections disclosed herein.

1. A method of treatment of a patient suffering from a viral infection (e.g., a retrovirus, a respiratory virus or a hepatitis C virus infection) or having a common cold, comprising administering to said patient an effective amount of at least one compound of formula 1 or 2.

2. A method according to embodiment 1, wherein said at least one compound is naringin, naringenin or a derivative (e.g., an ester) that can convert to either in vivo.

3. A method of reducing at least one aminotransferase level in a patient suffering from hepatitis virus C, comprising administering to said patient an effective amount of at least one compound of formula 1 or 2.

4. A method according to embodiment 3, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

5. A method of treatment of a patient suffering from a togavirus, comprising administering to said patient an effective amount of at least one compound of formula 1 or 2.

6. A method according to embodiment 5, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

7. A method according to embodiment 5, wherein said togavirus is an alphavirus.

8. A method according to embodiment 5, wherein said togavirus is a flavivirus.

9. A method according to embodiment 8, wherein said flavivirus is hepatitis G.

10. A method according to embodiment 8, wherein said flavivirus is yellow ever.

11. A method according to embodiment 5, wherein said togavirus is a rubivirus.

12. A method according to embodiment 11, wherein said rubivirus is rubella.

13. A method according to embodiment 5, wherein said togavirus is a pestivirus.

14. A method according to embodiment 13, wherein said pestivirus is BVDV.

15. A method according to any of embodiments 1–14, further comprising administering to said patient ribavirin and/or alpha interferon.

16. A pharmaceutical composition comprising (a) at least one compound of formula 1 or 2 and (b) ribavirin and/or alpha interferon.

17. A method of preventing disease caused by one or more liver parasite and/or minimizing the likelihood of onset of disease caused by one or more liver parasite and/or minimizing the adverse effects of future contact with one or more liver parasite, comprising administering to a patient an effective amount of at least one compound of formula 1 or 2.

18. A method according to embodiment 17, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

19. A method of (1) treating a patient suffering from malaria (e.g., *Plasmodium falciparum* or *Plasmodium vivax*, where the Plasmodium parasite is drug [e.g., chloroquine] resistant or drug sensitive) or (2) ameliorating one or more symptoms associated with malaria, comprising administering to said patient an effective amount of at least one compound of formula 1 or 2.

20. A method according to embodiment 19, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

21. A method of prophylactic treatment of a patient against malaria, comprising administering to said patient an effective amount of at least one compound of formula 1 or 2.

22. A method according to embodiment 21, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

23. A method of treatment of a patient suffering from common cold, comprising administering to said patient an effective amount of at least one compound of formula 1 or 2.

24. A method according to embodiment 23, wherein said at least one compound is naringin, naringenin or a derivative (e.g., an ester) that can convert to either in vivo.

25. A method according to embodiment 23 or embodiment 24, wherein said administering is through nasal route.

26. A method of prophylactic treatment of a patient against common cold, comprising administering to said patient an effective amount of at least one compound of formula 1 or 2.

27. A method according to embodiment 26, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

28. A method according to embodiment 23 or embodiment 24, wherein said administering is through nasal route.

29. A method of treatment of a patient suffering from influenza, comprising administering to said patient an effective amount of at least one compound of formula 1 or 2.

30. A method according to embodiment 29, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

31. A method according to embodiment 29 or embodiment 30, wherein said administering is through nasal route.

32. A method of prophylactic treatment of a patient against influenza, comprising administering to said patient an effective amount of at least one compound of formula 1 or 2.

33. A method according to embodiment 32, wherein said at least one compound is one or more of cirsiliol, tangeretin, gossypetin, naringenin, naringin or a derivative of any of these compounds that can convert in vivo to cirsiliol, tangeretin, gossypetin, naringenin or naringin.

34. A method according to embodiment 32 or embodiment 33, wherein said administering is through nasal route.

35. The method of any of embodiments 1–34 wherein the formula 1 or 2 compound is acacetin [reg. no. 480-44-4], apigenin [reg. no. 520-36-5], apiin [reg. no. 26544-34-3], baicalein [reg. no. 491-67-8], baicalein trimethyl ether [5,6,7-trimethoxyflavone], 5,6-benzoflavone [reg. no. 6051-87-2], 7,8-benzoflavone [reg. no. 604-59-1], 8-carboxy-3-methylflavone [reg. no. 3468-01-7], dihydrorobinetin [reg. no. 4382-33-6], 3,7-dihydroxy-3',4'-dimethoxyflavone [fisetin 3'4'-dimethylether], 3,5-dihydroxyflavone [reg. no. 6665-69-6], 3,6-dihydroxyflavone, 3,7-dihydroxyflavone [reg. no. 492-00-2], 3,2'-dihydroxyflavone, 3,3'-dihydroxyflavone, 5,7-dihydroxyflavone [chrysin], 5,2'-dihydroxyflavone, 5,3'-dihydroxyflavone, 5,4'-dihydroxyflavone, 6,7-dihydroxyflavone [reg. no. 38183-04-9], 6,2'-dihydroxyflavone, 6,3'-dihydroxyflavone, 6,4'-dihydroxyflavone, 7,8-dihydroxyflavone, 7,2'-dihydroxyflavone, 7,3'-dihydroxyflavone, 7,4'-dihydroxyflavone, 2',3'-dihydroxyflavone, 2'4'-dihydroxyflavone, 3',4'-dihydroxyflavone [4-hydroxyflavanol], 5',6'-dihydroxy-7-methoxyflavone [reg. no. 29550-13-8], 5',4'-dihydroxy-7-methoxyflavone [reg. no. 437-64-9], 3',4'-dihydroxy-α-napthoflavone, 3',4'-dihydroxy-β-napthoflavone, 5',8'-dihydroxy-3,7,3',4'-tetramethoxyflavone [reg. no. 7380-44-1], gossypetin 3,7,3'4'-tetramethylether], 3,7'-dihydroxy-3,4,5'-trimethoxyflavone [robinetin trimethylether], 5,3'-dihydroxy-6,7,4'-trimethoxyflavone [eupatorin], 3,5'-dimethoxyflavone, 3,6-dimethoxyflavone, 3,7'-dimethoxyflavone, 3,2'-dimethoxyflavone, 3,3'-dimethoxyflavone, 3,4'-dimethoxyflavone, 5,7-dimethoxyflavone [reg. no. 21392-57-4 chrysin dimethylether], 5,2'-dimethoxyflavone, 5,3'-dimethoxyflavone, 5,4'-dimethoxyflavone, 25 6,7'-dimethoxyflavone, 6,2'-dimethoxyflavone, 6,3'-dimethoxyflavone, 6,4'-dimethoxyflavone, 7,8'-dimethoxyflavone, 7,2'-dimethoxyflavone, 7,3'-dimethoxyflavone, 7,4'-dimethoxyflavone, 2,3'-dimethoxyflavone, 2,4'-dimethoxyflavone, 3,4'-dimethoxyflavone, 3-hydroxy-3,4-dimethoxyflavone, 3,4'-dimethoxy-α-naphthoflavone, 3,4'-dimethoxy-β-napthoflavone, 6,7'-dimethoxy-5,3',4'-trihydroxyflavone [reg. no. 34334-69-5; cirsiliol], 3,4'-dimethoxy-5,7',3'-trihydroxyflavone [reg. no. 33429-83-3], diosmetin [reg. no. 520-34-3], diosmetin-7-rutinoside [reg. no. 520-27-4; diosmin], eupatorin-5-methyl ether [3'-hydroxy-4',5,6,7-tetramethoxyflavone], 3,7,3',4'-tetrahydroxyflavone [reg. no. 528-43-31; fisetin], flavone [reg. no. 525-82-6], fortunellin [reg. no. 20633-93-6], 3,5,7-trihydroxyflavone [reg. no. 548-83-4; galangin ], 6,7,8,3',4',5'-hexamethoxy-5-hydroxyflavone [reg. no. 21187-73-5; gardenin A], geraldol [reg. no. 21511-25-1], 3,5,6,7,3',4'-hexahydroxyflavone [gossypetin], 3,5,7,8,3',4'-hexahydroxyflavone-8-glucoside [gossypin], 5,6,7,3',4',5'-hexamethoxyflavone [reg. no. 29043-07-0], 6-hydroxyapigenin [reg. no. 529-53-3; scutellarein], 3-hydroxy-6,4'-dimethoxyflavone, 5-hydroxy-7,4'-dimethoxy-6,8-dimethylflavone [reg. no. 3122-88-1; eucalyptin], 3-hydroxyflavone [reg. no. 577-85-5; flavonol], 5-hydroxyflavone [reg. no. 491-78-1; primuletin], 6-hydroxyflavone [reg. no. 6665-83-4], 7-hydroxyflavone [reg. no. 6665-86-7], 2'-hydroxyflavone, 3'-hydroxyflavone, 4'-hydroxyflavone, 3-hydroxy-5-methoxyflavone, 3-hydroxy-6-methoxyflavone, 3,4'-dihydroxy-6-methoxyflavone, 3-hydroxy-7-methoxyflavone [reg. no. 7478-60-6; 7-methoxyflavanol], 3-hydroxy-2'-methoxyflavone, 3-hydroxy-3'-methoxyflavone, 6'-hydroxy-7-methoxyflavone, 6'-hydroxy-2'-methoxyflavone, 6'-hydroxy-3'-methoxyflavone, 6'-hydroxy-4'-methoxyflavone, 7'-hydroxy-2'-methoxyflavone, 7'-hydroxy-3'-methoxyflavone, 7'-hydroxy-2'-methoxyflavone [pratol], 5'-hydroxy-7-methoxyflavone, 4'-hydroxy-5-methoxyflavone, 4'-hydroxy-6-methoxyflavone, 2'-hydroxy-α-naphthoflavone, 2'-hydroxy-β-naphthoflavoneflavone, 4'-hydroxy-α-naphthoflavone, 4'-hydroxy-β-naphthoflavone, 5-hydroxy-3,3',4',7-tetramethoxyflavone [reg. no. 1254-15-4; quercetin tetramethylether], 3'-hydroxy-5,6,7,4'-tetrarnethoxyflavone [reg. no. 21764-09-0], isoquercitrin [reg. no. 21637-25-2; quercetin-3-glucoside], isorhamnetin [reg. no. 418-19-3], isorhamnetin-3-glucoside, isorhamnetin-3-rutinoside [reg. no. 604-80-8; narcisin], kaempferol [reg. no. 520-180-3; 3,5,7,4'-tetrahydroxyflavone], kaempferol-3,7,4'-trimethyl ether [reg. no. 15486-34-7], karanjin 521-88-0], luteolin [reg. no. 491-70-3], lutolin-4'-glucoside [reg. no. 62920-38-3], luteolin-7-glucoside [reg. no. 5373-11-5], 4'-methoxy-5,6-benzoflavone, 3-methoxyflavone [reg. no. 7245-02-5], 5-methoxyflavone [reg. no. 42079-78-7], 6'-methoxyflavone 26964-24-9], 7-methoxyflavone [reg. no. 222395-22-8], 2'-methoxyflavone [reg. no. 19725-47-4], 3'-methoxyflavone, 4'-methoxyflavone [reg. no. 4143-74-2], 5-methoxyflavone, 3-hydroxy-5-methoxyflavone, 6-methoxyflavone [reg. no. 26964-24-9], 3-hydroxy-6-methoxyflavone, 4'-methoxyflavone [reg. no. 7478-60-6], 3-hydroxy-7-methoxyflavone, 6-methoxyluteolin, 2'-methoxy-α-naphthoflavone [2'-methoxy-7,8-benzoflavone], 2'-methoxy-β-naphthoflavone [2'-methoxy-5,6-benzoflavone], 4'-methoxy-α-naphthoflavone, 4'-methoxy-β-naphthoflavone, 6-methylflavone [reg. no. 29976-75-8], 8-methylflavone, 6-methyl-4'-methoxyflavone, 8-methyl-4'-methoxyflavone, morin dihydrate [reg. no. 480-16-0], myricetin [reg. no. 529-44-2; 3,5,7,3'4',5'-hexahydroxyflavone], myricetin-3-rhamnoside [reg. no. 17912-87-72], naringin, naringenin, neodiosmin [diosmetin-7-neohesperidioside], 3,7,3',4',5'-pentamethoxyflavone [reg. no. 490-31-3; robinetin], 3,7,3',4',5'-pentahydroxyflavone, 5,6,7,3',4'-pentamethoxyflavone [reg. no. 2306-27-6; sinensetin], 3,6,7',3',4'-pentamethoxyflavone, 5,7,3',4',5'-pentamethoxyflavone, quercetagetin [reg. no. 90-18-6], quercitrin [reg. no. 522-12-3; quercitrin-3-rhamnoside], 3,5,7,3',4'-pentamethoxyflavone [reg. no. 1247-97-8; quercetin 3,5,7,3',4'-pentamethyl ether], 3,7,3',4'-tetramethoxyflavone [reg. no. 1245-15-4; retusin; quercetin-3,7,3',4'-tetramethyl ether], rutin trihydrate [reg. no. 153-18-4], 5,6,7,4'-tetramethoxyflavone [reg. no. 1168-42-9; scutellarein tetramethyl ether], spiraeoside [reg. no. 20229-56-5], tangeretin [reg. no. 481-53-8], 3,5,7,4'-tetrahydroxy-3',5'- dimethoxyflavone [reg. no. 4423-37-4; syringetin], 3,5,3',4'-tetrahydroxy-7-methoxyflavone 90-19-7; rhamnetin], 7,8,3'4'-tetrahydroxyflavone, 5,7,3',4'-tetramethoxyflavone [reg. no. 855-97-0; luteolin tetramethyl ether], 7,8,3',4'-tetramethoxyflavone [reg. no. 855-97-0], 3,6,4'-trihydroxyflavone, 3,7,4'-trihydroxyflavone [reg. no. 2034-65-3; 5-deoxykampferol], 3,3',4'-trihydroxyflavone, 5,7,8-trihydroxyflavone [reg. no. 4443-09-8], 5,7,2'-trihydroxyflavone [reg. no. 73046-40-9], 5,3',4'-tetrahydroxy-3',5'-dimethoxyflavone [reg. no. 4423-37-4], 6,3',4'-trihydroxyflavone, 7,8,2'-trihydroxyflavone, 7,8,3'-trihydroxyflavone, 7,8,4'-trihydroxyflavone, 7,3',4'-trihydroxyflavone [reg. no. 2150-11-0], 3,5,7-trihydroxy-3',4',5'-trimethoxyflavone [myricetin trimethyl ester], 5,7,4'-trihydroxyflavone [reg. no. 5631-70-9], 3,5,7-trimethoxyflavone, vitexin-2"-O-rhamnoside [reg. no. 64820-99-1], 2-(3,4-dibenzyloxy)-4,5,6-trimethoxyacetophenone, 3',4'-dibenzyloxy-2-hydroxy-4,5,6-trimethoxydibenzoylmethane, 3',4'-dibenzyloxy-5,6,7-trimethoxyflavone, 3',4'-dihydroxy-5,6,7-trimethoxyflavone, 3',4'-diacetoxy-5,6,7-trimethoxyflavone, 3-(4'-bromophenyl)-6-methoxycoumarin, 3-(4'-bromophenyl)-7-methoxy-4-methyl coumarin, 3-(4'-bromophenyl)-7-methoxy-4-phenylcoumarin, 3-(4'-bromophenyl) coumarin, 3-(4'-bromophenyl)-6,8-dichloro-4-methylcoumarin, 3-(4'-bromophenyl)-7-hydroxy-4-methylcoumarin, 6-bromo-3-(4'-chlorophenyl)-4-methylcoumarin, 6-bromo-4-(4'-chlorophenyl)-3-phenylcoumarin, 6-bromo-3,4-di-(4'-chlorophenyl) coumarin, 6-bromo-3-(2,4-dichlorophenyl)-4-methylcoumarin, 6-bromo-3,4-diphenylcoumarin, 6-methoxy-4-methylcoumarin, 6-methoxy-4-methyl-3-phenylcoumarin, 7-methoxy-4-methyl-3-phenylcoumarin, 6-methoxy-3-(4'-nitrophenyl)coumarin, 6-bromo-3-(4'-methoxyphenyl)-4-methylcoumarin, 3-(4'-bromophenyl)-6-chloro-4,7-dimethylcoumarin, 3-(4'-bromophenyl)-6-chloro-4-methlycoumarin, 6-chloro-3(2-chlorophenyl)-4-methylcoumarin, 6-chloro-3-(4'-chlorophenyl)-4-methylcoumarin, 3-(4'-methoxyphenyl)-4-methylcoumarin, 6-methyl-3-(4-methoxyphenyl)-4-phenylcoumarin, 3-(4'-nitrophenyl)coumarin, 6-methoxy-3-(4-methoxyphenyl)-4-methylcoumarin, 7-methoxy-3-(4'-methoxyphenyl)-4-methylcoumarin, 7-methoxy-3-(4'-methoxyphenyl)-4-phenylcoumarin, 3-(4'-methoxyphenyl)coumarin, 6-methoxy-3-phenylcoumarin, 7-methoxy-3-phenylcoumarin, 6,8-dichloro-3-2,4-dichlorophenyl)-4-phenylcoumarin, 6,8-dichloro-3,4-diphenylcoumarin, 6,8-dichloro-3-(4'methoxyphenyl)-4-methylcoumarin, 6,8-dichloro-3-(4'methoxyphenyl)-4-phenylcoumarin, 3-(2,4-dichlorophenyl)coumarin, 3-(2,4-dichlorophenyl)-4,6-dimethylcoumarin, 3-(2,4-dichlorophenly)-7-ethoxycoumarin, 3-(2,4-dichlorophenyl)-7-hydroxycoumarin, 3-(2,4-dichlorophenyl)-6-hydroxy4-methylcoumarin, 3-(2,4-dichlorophenyl)-7-hydroxy4-methylcoumarin, 3-(2,4-dichlorophenyl)-6-ethoxy-4-methylcoumarin, 3-(2,4-dichlorophenyl)-7-ethoxy-4-methylcoumarin, 3-(2,4-dichlorophenyl)-7-ethoxy-4-phenylcoumarin, 3-cyano-6-methoxycoumarin, 3-cyano-7-methoxycoumarin, 6,8-dichloro-3 (2,4-dichlorophenyl)-4-methylcoumarin, 3-(4'-chlorophenyl)-4-methylcoumarin, 3-cyano-7-ethoxy coumarin, 3-cyano-7-hydroxycoumarin, 3-cyano-7-hydroxy-4-methylcoumarin, 3-(2-chlorophenyl)-7-methoxy-4-phenylcoumarin, 3-(4'-chlorophenyl)-7-methoxy-4-phenyl coumarin, 3-(2-chlorophenyl)-4-methylcoumarin, 3-(2-chlorophenyl)-7-methoxycoumarin, 3-(4'-chlorophenyl)-7-methoxy coumarin, 3-(2-chlorophenyl)-7-methoxy-4-methylcoumarin, 3-(4'-chloropheny)-7-methoxy-4-methyl coumarin, 3-(2-chlorophenyl)-7-hydroxy-4-phenylcoumarin, 3-(4'chlorophenyl)-7-hydroxy-4-phenyl coumarin, 3-(4'-chlorophenyl)-6-methoxy coumarin, 3-(4'-chlorophenyl)-7-hydroxycoumarin, 3-(2-chlorophenyl)-7-hydroxy-4-methylcoumarin, 3-(4'-chlorophenyl)-7-hydroxy-4-methyl coumarin, 3-(2-chlorophenyl)-7-ethoxy-4-methylcoumarin, 3-(2-chlorophenyl)-7-ethoxy-4-phenylcoumarin, 3-(2-chlorophenyl)-7-hydroxycoumarin, 4-(4-chlorophenyl)-3-(2,4-dichlorophenyl)-6-methylcoumarin, 3-(2-chlorophenyl)-4,6-dimethylcoumarin, 3-(2-chlorophenyl)-7-ethoxycoumarin, 3-(4'-chlorophenyl)-7-ethoxycoumarin, 3-(2-chlorophenyl)-6,8-dichloro-4-methylcoumarin, 3-(4'-chlorophenyl)-6,8-dichloro-4-methyl coumarin, 4-(4'-chlorophenyl)-6,8-dichloro-3-phenyl coumarin, 6-chloro-3-(4'-methoxyphenyl)-4-phenyl coumarin, 6-chloro-4-methyl-3-(4'-nitrophenyl) coumarin, 3-(2-chlorophenyl) coumarin, 7-hydroxy-3-(4'-methoxyphenyl)-4-methylcoumarin, 7-hydroxy-3-(4'methoxyphenyl)-4-phenyl coumarin, 6-hydroxy-4-methyl-3-phenylcoumarin, 6-ethoxy-4-methylcoumarin, 6-ethoxy-4-methyl-3-phenyl coumarin, 7-hydroxy-3-(4'-methoxyphenyl) coumarin, 6-hydroxy-3-(4-methoxyphenyl)-4-methylcoumarin, 6-ethoxy-3(4-methoxyphenyl)-4-methylcoumarin, 7-ethoxy-3-(4'-methoxyphenyl)-4-methyl coumarin, 7-ethoxy-3-(4'methoxyphenyl)-4-phenyl coumarin, 4,6-dimethyl-3-(4-methoxyphenyl)coumarin, 3,4-diphenyl-7-methoxy coumarin, 3,4-diphenyl-6-methyl coumarin, 7-ethoxy-3-(4'methoxyphenyl) coumarin, 3,4-diphenyl-7-hydroxy coumarin, 3-(2,4-dichlorophenyl)-7-hydroxy-4-phenylcoumarin, 3-(2,4-dichlorophenyl)-7-methoxycoumarin, 3-(2,4-dichlorophenyl)-6-methoxy-4-methylcoumarin, 3-(2,4-dichlorophenyl)-7-methoxy-4-methylcoumarin, 3-(2,4-dichlorophenyl)-7-methoxy-4-phenylcoumarin, 3-(2,4-dichlorophenyl)-4-methylcoumarin, 6-chloro-3-formyl-7-methylcoumarin, 6-chloro-3(4'-methoxyphenyl)-4-methyl coumarin, 6-chloro-3(4'-methoxyphenyl)-7-methyl-4-phenyl coumarin, 6-chloro-4,7-dimethyl-3(4'-methoxy phenyl) coumarin, 6-chloro-3,4-diphenyl coumarin, 6-chloro-3,4-diphenyl-7-methyl coumarin, 6-chloro-3,4-di(4'-chlorophenyl)-7-methyl coumarin, 6-chloro-3 (2,4-dichlorophenyl)-7-methyl-4-phenylcoumarin, 6-chloro-3 (2,4-dichlorophenyl)-4-phenylcoumarin, 6-chloro-3-(2-chlorophenyl)-7-methyl-4-phenylcoumarin, 6-chloro-3 (2-chlorophenyl)-4-phenylcoumarin, 6-chloro-4(4'-chlorophenyl)-3-phenyl coumarin, 6-chloro-3,4-di(4'-chlorophenyl) coumarin, 6-chloro-3-(2,4-dichlorophenyl)-4,7-dimethyl coumarin, 6-chloro-3-(2 ,4-dichlorophenyl)-4-methylcoumarin, 6-chloro-3-(4'-chlorophenyl)-4,7-dimethylcoumarin, 6-chloro-4-(4'-chlorophenyl)-3 (4'methoxy phenyl)coumarin, 6-chloro-4-(4'-chlorophenyl)-3-(4'methoxy phenyl)-7-methylcoumarin, 6-chloro-4-(4-chlorophenyl)-3-(2,4-dichlorophenyl)coumarin, 6-chloro-4-(4-chlorophenyl)-3 (2,4-dichlorophenyl)-7-methylcoumarin, 6-chloro-3-(2-chlorophenyl)-4,7-dimethylcoumarin, 6-chloro-3-(2-chlorophenyl)-4-methylcoumarin, 6-chloro-3-(4'-chlorophenyl)-4-methyl coumarin, 7-hydroxy-4-methyl-3-phenyl coumarin, 7-hydroxy-3-phenyl coumarin, 6-methoxy-3-(4'-methoxyphenyl) coumarin or 7-methoxy-3-(4'-methoxyphenyl) coumarin.

36. The method of any of embodiments 1–35 further comprising administering one or more known anti-infective or therapeutic agents, e.g., an analgesic (aspirin, acetaminophen, etc.), a compound selected from nucleoside analogs (AZT, 3TC, ddI, ddC, D4T, etc.), protease inhibitors (indinavir, crixivan, nelfinavir), chloroquine, ribavirin, amanditine, rimantadine, oseltamivir, zanamivir, IL-2, γ-interferon and α-interferon, wherein the anti-infective or therapeutic agent is administered simultaneously (within about 2 hours of administration of the formula 1 or 2 compound) or before (at least about 4–48 hours before administration of the formula 1 or 2 compound) or after (at least about 4–48 hours after administration of the formula 1 or 2 compound) administration of the formula 1 or 2 compound.

37. A product produced by the process of contacting a formula 1 or 2 compound and an excipient.

38. Use of a compound of formula 1 or 2 to prepare a medicament for use to treat or prevent an infection or to ameliorate one or more symptoms associated with an infection in a subject.

39. The use of embodiment 38 wherein the formula 1 or 2 compound is a compound named in embodiment 35.

40. The use of embodiment 38 or 39 wherein the infection is a viral infection or a parasite infection.

41. The use of embodiment 40 wherein the subject is a human.

42. The use of embodiment 38, 39, 40 or 41 wherein the formula 1 or 2 compound is cirsiliol or a derivative that can convert to cirsiliol in vitro or in vivo.

43. The use of embodiment 42 wherein the subject has a common cold.

44. A method comprising administering to a subject having an infection an effective amount of a composition comprising an acceptable excipient and one or more compounds of formula 1 or 2.

45. The method of embodiment 44 wherein 1, 2, 3, 4, 5 or 6 $R_8$ are independently selected moieties other than hydrogen, i.e., they are not hydrogen.

46. The method of embodiment 44 or 45 wherein $R_8$ are independently selected —OH, halogen, $C_{1-6}$ alkyl, $C_{1-6}$ alkoxy, glucuronide, a moiety that can hydrolyze to hydroxyl, a $C_{1-25}$ fatty acid, glucoside, or a group having structure (B) or (C).

47. The method of embodiment 44, 45 or 46 wherein the infection is a virus infection, which is optionally selected from the group consisting of a respiratory syncytial virus infection, a paramyxoviridae family virus infection, an orthomyxovirus infection, an influenza virus infection, a parainfluenza virus infection, a retrovirus infection, a hepatitis virus infection, a rhinovirus infection, a pneumovirus infection, a herpesvirus infection, an enterovirus infection or a coronavirus infection.

48. The method of embodiment 44, 45 or 46 wherein the infection is a parasite infection, which is optionally selected from the group consisting of toxoplasmosis parasite, trypanosome parasite and plasmodium parasite infections.

49. The method of embodiment 47 or 48 wherein the formula 1 or 2 compound is a compound named in embodiment 35.

50. A method of treating or preventing the common cold or of ameliorating one or more symptoms of a common cold comprising administering to a subject having a common cold or susceptible to a common cold an effective amount of a composition comprising a pharmaceutically acceptable carrier and a compound of formula 1 or 2.

51. The method of embodiment 50 wherein the formula 1 or 2 compound is cirsiliol or a derivative of cirsiliol than can convert to cirsiliol in vitro or in vivo.

52. The method of embodiment 50 or 51 wherein the subject has a rhinovirus infection.

53. A method to decrease expression of TNF, IL-1 or IL-2 in a subject having an common cold or influenza infection comprising administering to the subject an effective amount of a formula 1 or 2 compound or a derivative thereof than can convert to the formula 1 or 2 compound in vitro or in vivo, wherein the modulation is detectably enhanced expression of TNF, IL-1 or IL-2.

54. The method of embodiment 53 wherein the infection is a common cold.

55. The method of embodiment 54 wherein the formula 1 or 2 compound is cirsiliol or a derivative thereof than can convert to cirsiliol in vitro or in vivo.

56. A method of treating or preventing an infection caused by a virus in the Picornavirus genus comprising administering to a subject having or susceptible to a Picornavirus infection an effective amount of a composition comprising a pharmaceutically acceptable carrier and a compound or formula 1 or 2.

57. The method of embodiment 56 wherein the formula 1 or 2 compound is cirsiliol or a derivative of cirsiliol than can convert to cirsiliol in vitro or in vivo.

58. The method of embodiment 56 or 57 wherein the subject has an infection caused by a rhinovirus, a poliovirus, a cardiovirus, a parechovirus, a hepatovirus, an enterovirus or an aphthovirus.

59. The method of embodiment 56 wherein the formula 1 or 2 compound is one or more of cirsiliol, tangeretin, gossypetin, naringenin, naringin or a derivative of any of these compounds that can convert in vivo to cirsiliol, tangeretin, gossypetin, naringenin or naringin.

60. A method of treating, preventing or ameliorating one or more symptoms associated with a viral or parasite infection in a subject comprising administering to the subject a formula 1 or 2 compound, which is optionally one or more of cirsiliol, tangeretin, gossypetin, naringenin, naringin or a derivative of any of these compounds that can convert to the formula 1 or 2 compound or to cirsiliol, angeretin, gossypetin, naringenin or naringin, wherein the viral or parasite infection is a toxoplasmosis infection, a neumovirus infection, a lower respiratory tract infection, an otitis media infection, a bronchiolitis infection, a viral pneumonia infection, a rhinovirus infection, an enterovirus infection, a coronavirus infection, an adenovirus infection, an influenza A or B virus infection, a herpesvirus infection, a hepatitis virus infection, an orthomyxovirus infection, a retrovirus infection, a toxoplasma infection, a cryptosporidium infection (e.g., a Cryptosporidium parvum) or a malaria infection.

61. The method of embodiment 60 wherein the formula 1 or 2 compound is administered intravenously and/or intraperitoneally and/or subcutaneously and/or intramuscularly and/or orally and/or topically and/or by aerosol.

62. The method of embodiment 60 or 61 wherein the formula 1 or 2 compound is administered intraperitoneally or intramuscularly or subcutaneously in a range of about 0.01 to about 30 mg/kg or orally in a range of about 0.10 to about 50 mg/kg.

63. A method of treating the common cold or related disorders selected from the group consisting of sinusitis, otitis, influenza, and infectious exacerbations of chronic obstructive pulmonary disease, or a method of treating or ameliorating one or more symptoms associated with toxoplasmosis or malaria, comprising administering to a patient in need thereof a therapeutically effective amount of (1) at least one compound of formula 1 or 2 or a compound named in embodiment 35 and (2) an antiviral or antiparasite agent specific for a virus or parasite which causes the common cold selected from the group consisting of including rhinoviruses, adenoviruses, enteroviruses, coronaviruses, respiratory syncytial viruses, influenza viruses and parainfluenza viruses.

64. A metered dose inhaler having an aerosol composition (useful for, e.g., for combating the common cold, sinusitis, otitis, influenza, a lower respiratory tract infection and infectious exacerbations of chronic obstructive pulmonary disease), the aerosol composition comprising a propellant and a compound of claim 1.

65. A compound of formula 1 or 2 or a salt or hydrate thereof.

66. A composition comprising an effective amount of a compound of formula 1 or 2 or a salt or hydrate thereof and an excipient or a pharmaceutically acceptable carrier.

67. The composition of embodiment 66 wherein the composition comprises a unit dosage form, wherein the unit dosage form is optionally selected from a tablet, a capsule, a powder (suitable, e.g., for aerosol delivery of the compound) or a liquid.

68. The compound or composition of embodiment 65, 66 or 67 wherein the formula 1 or 2 compound is a compound or genus or group of compounds that is named or disclosed herein.

69. The compound or composition of embodiment 68 wherein the formula 1 or 2 compound comprises one, two or three —SH or =S moieties at one, two or three independently selected $R_8$, $R_{10}$ or $R_{11}$.

EXAMPLES

The following examples further illustrate the invention and are not to be construed as limiting the invention.

The following identifies the procedure used in a range of protocols, which establishes the efficacy of using compounds as disclosed herein. The data that establishes the efficacy is presented in the tables shown in table form.

Screening For Anti-influenza Efficacy. Compounds known to be active against the specific viruses will be used as positive control drugs. In this assay the positive control drug is Ribavirin for both Parainfluenza and Influenza A viruses CPE-Inhibition Assay Procedure. Mammalian cells are pregrown as monolayers in wells of 96-well tissue culture plates using suitable cell culture medium. Stock viruses are pretitered according to the method of Reed and Muench (Amer. J. Hyg. 27:493–497, 1938) and diluted in cell culture medium to yield 32- 100 CCID50 (cell culture infectious dose, 50%) units per 0.1 ml. Antiviral assays are designed to test six concentrations of each compound, preferably from cytotoxic to nontoxic levels, in triplicate against the challenge virus. To each of the replicate cell cultures are added 0.1 ml of the test drug solution and 0.1 ml of virus suspension. Cell controls containing medium alone, virus-infected cell controls containing medium, and drug cytotoxicity controls containing cells, medium and each drug concentration are run simultaneously with the test samples assayed in each experiment. The covered plates are incubated at 37° C. in a humidified atmosphere containing 5% $CO_2$ until maximum cytopathogenic effects (CPE) are observed in the untreated virus control cultures. CPE inhibition can be determined by microscopic examination or by a dye uptake (MTT) procedure.

Category 1. CPE-Inhibition (MTT) Assay (IV types A & B)

Category 2. CPE-Inhibition (Microscopic) Assay (PI-3, IV types A & B).

Protocol A1—Category 1—Method to quantitatively determine the degree of CPE inhibition and drug cytotoxicity. This method measures cell viability and is based on the reduction of the tetrazolium salt, 3-(4,5-dimethyl-thiazol-2-yl)-2,5-diphenyl tetrazolium bromide (MTT) by mitochondrial enzymes of viable host cells to MTT formazan. (T. Mosmann, J. Immunol. Methods. 65:55, 1983). Test and control cell cultures are treated with MTT followed by SDS to dissolve the crystals of MTT formazan. The antiviral assays are set up by the CPE-inhibition procedure described above except that two additional controls are included: (1) reagent control-culture medium only (no cells); and (2) drug calorimetric controls-drug+medium (no cells). When CPE in the untreated virus control wells reach 100%, the cultures are treated with MTT and SDS. The blue color of the MTT formazan is measured spectrophotometrically. The optical density (OD) value of each culture is a function of the amount of formazan produced which is proportional to the number of viable cells. A computer program is utilized to calculate the percent reduction of the virus-infected cultures and the % cell viability of uninfected drug control cultures, as well as other indices such as the IC50 (minimum inhibitory drug conc., 50%) and the Selectivity Index (minimum toxic concentration/$IC_{50}$).

Protocol A2 Category 2. The cell culture wells are examined microscopically for CPE and for drug cytotoxicity. Antiviral activity is determined by calculating the degree of inhibition of virus-induced CPE in drug-treated, virus-infected cell cultures by means of a virus rating (VR). The VR is a standard weighted measurement of antiviral activity taking into account both the degree of CPE inhibition and drug cytotoxicity, and is determined by a modification of the method of Ehrlich et al. (Ann. N.Y. Acad. Sci.130:5–16, 1965) as described below. CPE are graded for each individual culture in each microtiter plate well according to a scale of 0–4 (no CPE-100% CPE).

The VR is calculated as 0.1 of the sum of the numerical differences between the recorded CPE grades of each test well and that of the corresponding virus control in the culture plate. Numerical differences between the scores of test wells containing a drug concentration that is partially cytotoxic (p) and their corresponding virus controls are halved.

A VR of 1.0 or greater is indicative of significant antiviral activity with a high degree of reproducibility in confirmatory in vitro tests. Therefore, any compound with a VR of 1.0 or greater as active (+). Any compound with a VR of 0.5–0.9 is considered to have possible or marginal activity (+), and any compound with a VR of less than 0.5 is considered to be inactive (−) in the test system.

The minimum inhibitory drug concentration which reduces the CPE by 50% ($MIC_{50}$, or $ID_{50}$) is calculated by using a regression analysis program for semi log curve fitting. A therapeutic index (TI) for each active compound for each susceptible virus is determined by dividing the minimum cytotoxic concentration of the test compound by the $MIC_{50}$.

Protocol B—Screening for anti-picornaviral activity. Each compound is tested at 5 different concentrations, in duplicate against poliovirus type 1; Rhinovirus type 2 and Rhinovirus type 14 (minor and major type group viruses). The entire assay will be performed on two separate occasions. Confluent monolayers of BS-C-1 (African green monkey kidney) or HEL (human embryonic lung) cells will be infected with 0.1 plaque forming units (per cell) of the respective viruses for 1 hour, in the absence of drug, and the inoculum then replaced with fresh medium containing the drug for a further 12–24 h. Monolayers will be harvested (by freeze thawing) when the drug free controls show extensive cytopathic effects in 90–100% of the cells.

Virus yield from each of the control and treated cultures will be assayed by plaque assay in the absence of drug, and results presented as % infectious yield vs. concentration of drug.

Note that by using a multiplicity of infection of only 0.1 we will be able to detect effects at both early and late stages of virus replication, as the assay will cover two rounds of replication. Note also that this assay format differs from the commonly used "plaque reduction assay" in which the effect of the drug is measured directly in a plaque assay, resulting in reduced numbers of plaques. The plaque reduction assay may not detect some active drugs, since some drugs may reduce the number of plaques without making them undetectable.

Protocol C—In-vitro testing of anti Toxoplasma gondii activity of Cirsiliol and Naringin. The compounds were tested in an in vitro cell culture assay utilizing human fibroblasts (HFF line) as the host cell. RH strain Toxoplasma gondii that has been transfected with β-galactosidase as a marker for quantitative detection of parasite number (RH Bgal), was used as the challenge organism. The compounds ere dissolved, and then diluted in cell culture medium at least 100 fold for the assays. Controls containing the maximum concentration of solvent used in the assay were run with each test. The active drugs were added and the monolayers were infected immediately at the beginning of each test. Extracellular T. gondii were removed by rinsing the monolayer, and infected host cells remained in contact with the cells for the entire test period. Each test was terminated when at least four parasite doublings could be visually identified in the control monolayers, and parasite numbers were quantitated by standard colorimetric assay for bet galactosidase activity with optical density at 550 nm as the readout. The optical density in this assay has a direct and linear correlation with parasite numbers over a 5-log parasite concentration. Toxicity in the host cells was determined by inspection for cytopathic effects and visual evaluation of cell growth.

Protocol D1—Anti-HIV activity in fresh human cells—Assay in fresh human T-lymphocytes. Fresh human peripheral blood lymphocytes (PBL) are isolated from donors, seronegative for HIV and HBV. Leukophoresed blood is diluted 1:1 with Dulbeccos phosphate buffered saline (PBS), layered over 14 ml of FicollHypaque density gradient in a 50 ml centrifuge tube. Tubes are then centrifuged for 30 minutes at 600×g. Banded PBL's are gently aspirated from the resulting interface and subsequently washed 2× with PBS by low speed centrifugation. After final wash, cells are enumerated by trypan blue exclusion and resuspended at about $1 \times 10^7$/mL in RPMI 1640 with 15% Fetal Bovine Serum (FBS), 2 mM L-glutamine, 4 µ/ml PHA-P and allowed to incubate for 48 to 72 hours at 37° C. After incubation, the PBLs are centrifuged and reset in RPMI 1640 with 15% FBS, 2 mM L-glutamine, 100 U/mL penicillin, 100 µ/mL streptomycin, 10 µg/mL gentamycin and 20 U/mL recombinant human IL-2. PBL's are maintained in this medium at a concentration of $1-2 \times 10^6$/mL with bi-weekly medium changes, until used in assay protocol.

For the PBL assay, PHA-P stimulated cells from at least two normal donors are pooled, set in fresh medium at $2 \times 10^6$/ml and plated in the interior wells of a 96 well round bottom microplate at 50 µL/well. Test drug dilutions are prepared at a 2×concentration in microtiter tubes and 100 µL of each concentration is placed in appropriate wells in a standard format. 50 µL of a predetermined dilution of virus stock is placed in each test well. Wells with cells and virus alone are used for virus control. Separate plates are identically set without virus for drug cytotoxicity studies using an XTT assay system.

In the standard PBL assay (MOI: 0.2), the assay was ended on day 7 following collection of cell free supernatant samples for reverse transcriptase activity assay. Tritiated thymidine triphosphate (NEN)(TTP) was resuspended in distilled $H_2O$ at 5 Ci/mL. Poly rA and oligo dT were prepared as a stock solution which was kept at −20° C. The RT reaction buffer was prepared fresh on a daily basis and consists of 125 µL of 1M EGTA, 125 µL dH20, 110 µL 10% SDS, 50 µL 1M Tris (pH 7.4), 50 µL M DTT and 40 µL 1M $MgCl_2$. These three solutions were mixed together in a ratio of 2 parts TTP, 1 part poly rA: oligo dT and one part reaction buffer. Ten microliters of this reaction mixture was placed in a round bottomed microtiter plate and 15 µL of virus containing supernatant was added and mixed. The plate was incubated at 37° C. in a waterbath with a solid support to prevent submersion of the plate and incubated for 60 minutes.

Following reaction the reaction volume was spotted onto pieces of DE81 paper, washed 5 times for 5 minutes each in a 5% sodium phosphate buffer, 2 times for 1 minute each in distilled water, 2 times for 1 minute each in 70% ethanol and then dried. OptifluorO was added to each sample and incorporated radioactivity was quantitated utilizing a Wallac 1450 Microbetaplus liquid scintillation counter. Toxicity plates are stained with XTT as described above.

Protocol D2—Assay in fresh human monocyte-macrophages. For isolation of adherent cells, $3 \times 10^6$ non-PHA stimulated peripheral blood cells are resuspended in Hanks buffered saline (with calcium and magnesium) supplemented with 10% human AB serum. The cells are placed in a 96-well microtiter plate at 37° C. for 2 hours. Non-adherent cells are removed by vigorously washing six times. The adherent cells are cultured for 7 days in RPMI 1640 tissue culture medium with 15% fetal bovine serum. The cultures are carefully monitored for confluency during this incubation period. Infection of the cells is performed with monocytotropic HIV-1 isolates. High titer pools of each of these viruses are harvested from infected cultures of peripheral blood adherent cells and frozen in 1.0 ml aliquots at −80° C. Monocytemacrophage monolayers are infected at a multiplicity of infection ("MOI") of 0.1. Compounds to be evaluated in the monocyte macrophage assay are added to the monolayer shortly before infection in order to maximize the potential for identifying active compounds.

At 2 days post-infection, the medium is decanted and the cultures washed twice with complete medium in order to remove excess virus. Fresh medium alone or medium containing the appropriate concentration of drug is added and incubation continued for an additional five days. XTT staining for cytotoxicity and HIV p24 ELISA assays for production of p24 core antigen are performed on Day 7 post infection. This is performed according the ELISA kit assay manufacturers recommendations. Control curves are generated in each assay to accurately quantitate the amount of capsid protein in each sample. Data is obtained by spectrophotometric analysis at 450 nm using a Molecular Devices Vmax plate reader. P24 concentrations are calculated form the optical density values by use of the Molecular Device software package Soft Max.

The table below shows results obtained from various assays. For naringin tested against HIV Ba-L, the compound was solubilised in 30% or 95% ethanol as indicated. Most of the values were based on average values that were obtained from duplicate or triplicate assay wells.

| Compound | Parasite or Virus | Cell | Protocol | IC$_{50}$ ($\mu$m) | TC$_{50}$ ($\mu$m) | TI |
|---|---|---|---|---|---|---|
| 7,8-Benzoflavone | HIV Ba-L | macrophage | D2 | >200 | >200 | — |
| 3-(4'-Bromophenyl) coumarin | parainfluenza HA-1 | | A2 | 6.3 | 100 | 16 |
| Cirsiliol | Influenza A | MDCK | A2 | >200 | <6.3 | — |
| Cirsiliol | parainfluenza HA-1 | Hep2 | A2 | 7.8 | 12.5 | 1.6 |
| Cirsiliol | rhinovirus 14 | | B | ~3 | — | — |
| Cirsiliol | rhinovirus 14 | | B | ~3 | — | — |
| Cirsiliol | rhinovirus 14 | | B | ~3 | — | — |
| Cirsiliol | rhinovirus 14 | | B | ~3 | — | — |
| Cirsiliol | T, gondii RH | HFF | C | ~2 | — | — |
| Flavone | HIV ROJO | PBMC | D1 | 86.6 | 172.8 | 2.0 |
| Gossypetin | HIV ROJO | PBMC | D1 | 1.6 | 8.3 | 5.2 |
| Gossypetin | HIV ROJO | PBMC | D1 | 1.6 | 2.8 | 1.8 |
| Gossypetin | HIV Merck 52-52 | PBMC | D1 | 1.3 | 2.8 | 2.1 |
| Gossypetin | HIV Merck 144-44 | PBMC | D1 | 0.9 | 2.8 | 3.0 |
| Gossypetin | HIV Merck 1022-48 | PBMC | D1 | 0.8 | 2.8 | 3.4 |
| Gossypetin | HIV Merck 1002-60 | PBMC | D1 | 0.8 | 2.8 | 3.6 |
| Gossypetin | HIV Merck 1026-60 | PBMC | D1 | 2.5 | 2.8 | 1.1 |
| Gossypetin | HIV Merck 1064-52 | PBMC | D1 | 1.0 | 2.8 | 2.9 |
| Gossypetin | HIV clade A UG/93/037 | PBMC | D1 | 0.8 | 2.8 | 3.7 |
| Gossypetin | HIV clade B BR/92/014 | PBMC | D1 | 1.4 | 2.8 | 2.0 |
| Gossypetin | HIV clade E THA/93/073 | PBMC | D1 | 0.9 | 2.8 | 3.2 |
| Gossypetin | HIV clade F BR/92/021 | PBMC | D1 | 3.1 | 2.8 | — |
| Gossypetin >1.2 | HIV Ba-L | macrophage | D2 | 86.2 | >100 | |
| Gossypetin | rhinovirus 14 | | B | ~80 | — | — |
| Gossypetin | rhinovirus 14 | | B | >100 | — | — |
| Gossypetin | rhinovirus 14 | | B | ~70 | — | — |
| Gossypetin | rhinovirus 14 | | B | ~70 | — | — |
| Hesperetin | HIV ROJO | PBMC | D1 | 134.4 | 190.1 | 1.4 |
| Hydroxyflavone >3.1 | HIV Ba-L | macrophage | D2 | 63.8 | >200 | |
| 6-Hydroxyflavone | HIV ROJO | PBMC | D1 | 41.8 | 53.9 | 1.3 |
| Naringin | parainfluenza HA-1 | Hep2 | A2 | 25.0 | 100.0 | 4.0 |
| Naringin (35% EtOH) >1.2 | HIV Ba-L | macrophage | D2 | 86.2 | >100 | |
| Naringin (95% EtOH) | HIV Ba-L | macrophage | D2 | >100 | >100 | — |
| Naringin | T, gondii RH | HFF | C | >100 | — | — |
| Tangeretin | HIV ROJO | PBMC | D1 | 19.1 | 26.2 | 1.4 |
| Tangeretin | HIV ROJO | PBMC | D1 | 40.3 | 75.9 | 1.9 |
| Tangeretin | HIV Merck 52-52 | PBMC | D1 | 18.2 | 26.2 | 1.4 |
| Tangeretin | HIV Merck 144-44 | PBMC | D1 | 14.7 | 26.2 | 1.8 |
| Tangeretin | HIV Merck 1002-60 | PBMC | D1 | 9.7 | 26.2 | 2.7 |
| Tangeretin | HIV Merck 1022-48 | PBMC | D1 | 20.8 | 26.2 | 1.3 |
| Tangeretin | HIV Merck 1026-60 | PBMC | D1 | 19.8 | 26.2 | 1.3 |
| Tangeretin | HIV Merck 1064-52 | PBMC | D1 | 15.0 | 26.2 | 1.8 |
| Tangeretin | HIV clade A UG/93/037 | PBMC | D1 | 19.4 | 26.2 | 1.4 |
| Tangeretin | HIV clade B BR/92/014 | PBMC | D1 | 12.3 | 26.2 | 2.1 |
| Tangeretin | HIV clade E THA/93/073 | PBMC | D1 | 15.3 | 26.2 | 1.7 |
| Tangeretin | HIV clade F BR/92/021 | PBMC | D1 | 15.7 | 26.2 | 1.7 |

-continued

| Compound | Parasite or Virus | Cell | Protocol | IC$_{50}$ ($\mu$m) | TC$_{50}$ ($\mu$m) | TI |
|---|---|---|---|---|---|---|
| Tangeretin | HIV Ba-L | macrophage | D2 | >100 | >100 | — |
| Tangeretin | rhinovirus 14 | | B | ~70 | — | — |
| Tangeretin | rhinovirus 14 | | B | ~20 | — | — |
| Tangeretin | rhinovirus 14 | | B | ~60 | — | — |

HCV in vitro assays. No well-accepted model exists for HCV and new compounds for use in the treatment of HCV are frequently tested for activity against bovine viral diarrhea virus (BVDV), a virus which is related to HCV.

A representative compound according to the present invention, naringin (i.e., 7-neohesperidoside, 5, 4' dihydroxyflavanone) was tested for anti-BVDV activity in MDBK cells. As a comparison, similar tests were conducted using ribavirin. The results of these tests are shown in Tables A and B below. As can be seen from Tables A and B, in the case of the use of naringin (according to the present invention), the ID$_{50}$ was found to be 631 $\mu$M and the therapeutic index was found to be 3.17. For ribavirin, the ID$_{50}$ was 1.24 $\mu$M and the therapeutic index was 8.05. No cytotoxicity was observed with naringin at any concentration, the highest concentration tested being 2000 $\mu$M.

TABLE A

Effects of Naringin Upon Plaque Formation Produced by Bovine Viral Diarrhea Virus in MDBK Cultures

| naringin conc. | Number of plaques | | | |
|---|---|---|---|---|
| $\mu$g/mL | Test 1 | Test 2 | Test 3 | % Reduction |
| #9 2000.00 | 4 | 3 | 3 | 95.11 |
| #8 1500.00 | 8 | 11 | 8 | 86.82 |
| #7 1000.00 | 22 | 25 | 14 | 70.22 |
| #6 500.00 | 32 | 45 | 42 | 41.92 |
| #5 250.00 | 50 | 58 | 52 | 21.91 |
| #4 125.00 | 52 | 65 | 61 | 13.12 |
| #3 62.50 | 57 | 65 | 57 | 12.64 |
| #2 31.25 | 65 | 75 | 60 | 2.39 |
| #1 0.00 | 68 | 68 | 68 | 0 |

ID$_{50}$: 631.39 Tindx: 3.16 MTC: >2000
Control is an average of six wells (values ranged from 60–74)
Solvent: EtOH. Drug particles were observed at 2000–500 $\mu$g/mL
Abbreviations:
MTC = minimum cytotoxic drug concentration
Tindx = therapeutic index

TABLE B

Effects of Ribavirin Upon Plaque Formation Produced by Bovine Viral Diarrhea Virus in MDBK Cultures

| ribavirin conc. | Number of Plaques | | | |
|---|---|---|---|---|
| $\mu$g/mL | Test 1 | Test 2 | Test 3 | % Reduction |
| #5 10.000 | 0 | 0 | 0 | 100.00* |
| #4 3.200 | 4 | 4 | 5 | 93.65 |
| #3 1.000 | 36 | 42 | 47 | 38.99 |
| #2 0.320 | 55 | 62 | 59 | 14.10 |
| #1 0.000 | 68 | 68 | 68 | |

*Partial toxicity to the cells was observed with no toxicity at lower concentrations
ID$_{50}$: 1.24 Tindx: 8.05 MTC: >10
Control is an average of six wells (values ranged from 60–74)
Comment: Positive control drug. Drug was soluble in medium.

Human HCV clinical trial. A human patient suffering from hepatitis C virus was treated according to the following regimen: initial dosing beginning on Day 0 (see Table C), three times daily, the patient ingested 4 g of naringin orally, and then drank hot tea; in later days, the patient ingested, three times daily, 4 g of naringin mixed in hot tea. This patient also suffered from HIV infection.

The tables below, labeled part 1 through part 4, show data from this patients' bloodwork on Day 0 (when treatment according to this invention was initiated), Day 3 (3 days after Day 0), Day 6 (6 days after Day 0) and Day 9 (9 days after Day 0). In addition, the tables include data from this patients' bloodwork 72 days before Day 0 ("Day -72").

| PART 1 | Ref. Ranges | Day-72 | Day 0 | Day 3 | Day 6 |
|---|---|---|---|---|---|
| Glucose | 65–110 mg/dL | 125 | 76 | 98 | 93 |
| Creatinine | 0.5–1.2 mg/dL | | 0.5 | 0.5 | 0.5 |
| Bun/Creatinine Ratio | 10–28 | 22 | | | |
| SGOT | 1–45 u/L | 98 | 83 | 62 | 38 |
| SGPT | 1–45 u/L | | 112 | 102 | 62 |
| WBC | 4–11 x $10^3$ /mm$^3$ | 3.4 | 3.2 | 3.3 | 3.4 |
| RBC | 3.9–5.1 x $10^6$ /mm$^3$ | 4.8 | 4.7 | 4.71 | 4.6 |

-continued

| PART 1 | Ref. Ranges | Day-72 | Day 0 | Day 3 | Day 6 |
|---|---|---|---|---|---|
| Hemoglobin | 13.0–17.0 g/dL | 14.2 | 14 | 13.9 | 13.7 |
| Hematocrit | 36–46% | 41.6 | 41.7 | 40.5 | 40.1 |
| MCV | 82–97 cubic mic. | 87 | 88 | 86 | 88 |
| MCH | 27–34 picograms | 30 | 30 | 30 | 30 |
| MCHC | 32–36% | 34 | 34 | 34 | 34 |
| Platelet Count | 150–400 × $10^3$ /mm$^3$ | 104 | 96 | 104 | 112 |
| Metamyelocytes | | | 0 | | |
| Lymphocytes | 15–50% | 35 | 29 | 25 | 28 |

| PART 2 | Ref. Ranges | Day-72 | Day 0 | Day 3 | Day 6 |
|---|---|---|---|---|---|
| Bands | 0–5% | 0 | 0 | | |
| Monocytes | 0–10% | 8 | 5 | 10 | 6 |
| Eosinophils | 0–5% | 2 | 1 | 0 | 1 |
| Basophils | 0–5% | 1 | 0 | 1 | 1 |
| Specific Gravity | 1.005–1.035 | | | 1.024 | 1.017 |
| Color | | | | Yellow | Dark Yellow |
| Appearance | | | | Clear | Clear |
| pH | 4.5–7.5 | | | 5 | 6 |
| Glucose, Urine | Negative | | | Negative | Negative |
| Protein, Urine | Negative | | | Negative | Negative |
| Acetone, Urine | Negative | | | Negative | Negative |
| Occult Blood | Negative | | | Negative | Negative |
| Bilirubin | Negative | | | Negative | Negative |
| Leukocyte esterase | Negative | | | Negative | Negative |
| Nitrite | Negative | | | Negative | Negative |

| PART 3 | Ref. Ranges | Day-72 | Day 0 | Day 3 | Day 6 | Day 9 |
|---|---|---|---|---|---|---|
| Total Lymphs (% of WBC) | 20–50% | | 29 | 25 | 28 | |
| Direct Lymphocyte Count | 1100–3000 cells/mm$^3$ | | 928 | 825 | 952 | |
| Total T (CD3) | 51–87% | | 86 | 86 | 85 | |
| Total T (Absolute #) | 510–3240 #/µL | | 798 | 710 | 809 | |
| Helper T (CD4) | 31–59% | 25 | 34 | 22 | 23 | |
| Heiper T (Absolute #) | 537–1571 #/µL | 280 | 316 | 182 | 219 | |
| Suppressor T (CD8) | 13–33% | 60 | 58 | 60 | 59 | |
| Suppressor T (Abs. #) | 235–753 #/µL | 673 | 538 | 495 | 562 | |
| Helper/Suppressor | 1.2–3.8 | 0.4 | 0.6 | 0.4 | 0.4 | |
| % CD19 (Earliest B Cell) | 5–25% | | 9 | 7 | 9 | |
| Absolute CD19 | 75–700 /mm$^3$ | | 84 | 58 | 86 | |
| % Dual CD56/CD16 | 5–30% | | 3 | 5 | 4 | |
| Absolute NK cells | 30–3000 /mm$^3$ | | 28 | 41 | 38 | |
| Hepatitis C RNA ultraquant | <200 copies/mL | | 2,871,300 | 1,500,900 | 340,540 | 78,592 |
| Hepatitis C by PCR log 10 | | | 6.5 | 6.2 | 5.5 | 4.9 |

| PART 4 | Ref. Ranges | Day-72 | Day 0 | Day 3 | Day 6 |
|---|---|---|---|---|---|
| IgG Serum | 800–1800 mg/dL | | 1960 | 2290 | 2050 |
| IgA Serum | 90–450 mg/dL | | 72.5 | 77.1 | 83.6 |
| IgM Serum | 60–280 mg/dL | | 211 | 206 | 225 |
| Interferon Gamma | | | 0 | | |
| Interleukin-2 | <30 pg/mL | | <30 | | |
| Interleukin-4 | | | <30 | | |
| IL-10 Neutrophils | 50–70 FL | | 55 | 64 | 64 | 64 |

The patient's hepatitis C PCR ultraquant, SGOT and SGPT values are plotted in the Figure. As can be seen from Table C and the Figure, administration of naringin in accordance with the present invention provided drastic reduction in the patient's hepatitis C PCR values, as well as the patient's SGOT and SGPT values. These results would have been completely unexpected to those of skill in the art in view of contemporary knowledge.

Inhibition of rhinovirus release from infected cells. Cirsiliol was tested for its effect on rhinovirus infected cells by infecting cells with 20 PFU of rhinovirus 2, followed by addition of cirsiliol at 1 hour post infection. At time up to 10 hours post-infection, intracellular and extracellular virus was measured by plaque assay. Cirsiliol-treated cells generated lower levels of infectious intracellular and extracellular virions by about 5 to 50 fold compared to untreated control cells.

Inhibition of parasite levels in vivo. Mice ($C_{57}BL/6$) were infected with 20 toxoplasma cysts and then treated with cirsiliol or control vehicle (0.1% DMSO). After the treatment, the level of toxoplasma cysts in the brain was reduced (about 1.5–2 fold) by the cirsiliol treatment compared to the control. Also, all 8 cirsiliol treated mice survived toxoplasmosis infection, while over the 21-day post infection follow up period, 4 of 8 control (DMSO vehicle treated) mice died by 15 days post infection.

The invention disclosed herein is not to be limited in scope by the specific described embodiments, since these embodiments are intended as illustrations of aspects of the invention. Any equivalent embodiments are intended to be within the scope of this invention. Indeed, various modifications of the invention in addition to those shown and described herein will become apparent to those skilled in the art from the description. Such modifications are also intended to fall within the scope of the disclosure and the appended claims.

What is claimed is:

1. A method of treating a viral or parasitic infection comprising administering an effective amount of a composition comprising an acceptable excipient and one or more compounds selected from the group consisting of cirsiliol and derivatives, salts, stereoisomers, positional isomers, metabolites, tautomers, ionized forms and solvates of cirsiliol to a subject in need of such treatment.

2. The method of claim 1, wherein said derivatives contain one or more esters.

3. The method of claim 2, wherein said one or more esters have the form organic moiety-C(O)—O-cirsiliol or organic moiety-O—C(O)-cirsiliol.

4. The method of claim 3, wherein said organic moiety has one to fifty carbon atoms and zero to ten independently selected heteroatoms.

5. The method of claim 4, wherein said one to fifty carbon atoms are selected from the group consisting of $C_{1-20}$ alkyl moieties, $C_{2-20}$ alkenyl moieties, $C_{2-20}$ alkynyl moieties, aryl moieties, $C_{2-9}$ heterocycles and substituted derivatives thereof.

6. The method of claim 4, wherein said independently selected heteroatoms are selected from the group consisting of O, S, N, P and Si.

7. The method of claim 1, wherein said infection is a viral infection selected from the group consisting of a respiratory syncytial virus infection, a picornavirus genus viral infection, a paramyxoviridae family viral infection, an orthomyxovirus infection, an influenza virus infection, a parainfluenza virus infection, a retroviral infection, a hepatitis virus infection, a rhinovirus infection, a pneumovirus infection, a herpesvirus infection, an enterovirus infection, a coronavirus infection, a common cold, a lower respiratory tract infection, a bronchiolitis infection, a pneumonia infection, otitis media, sinusitis and an infectious exacerbation of chronic obstructive pulmonary disease.

8. The method of claim 7, wherein said retroviral infection is selected from the group consisting of HIV, FIV and SIV.

9. The method of claim 7, wherein said hepatitis virus infection is selected from the group consisting of HBV and HCV.

10. The method of claim 7, wherein said subject is a human.

11. The method of claim 7, wherein said composition is administered by one or more of the methods selected from the group consisting of intravenously, intraperitoneally, subcutaneously, intramuscularly, orally, topically and by aerosol.

12. The method of claim 11, wherein said composition is administered intraperitoneally, intramuscularly or subcutaneously in a range of about 0.01 to about 30 mg/kg or orally in a range of about 0.10 to about 50 mg/kg.

13. The method of claim 11, wherein said subject is a human.

14. The method of claim 1, wherein said infection is a parasite infection selected from the group consisting of a toxoplasma parasite infection, trypanosome parasite infection, and a plasmodia parasite infection.

15. The method of claim 14, wherein said subject is a human.

16. The method of claim 14, wherein said composition is administered by one or more of the methods selected from the group consisting of intravenously, intraperitoneally, subcutaneously, intramuscularly, orally, topically and by aerosol.

17. The method of claim 16, wherein said composition is administered intraperitoneally, intramuscularly or subcutaneously in a range of about 0.01 to about 30 mg/kg or orally in a range of about 0.10 to about 50 mg/kg.

18. The method of claim 16, wherein said subject is a human.

19. The method of claim 1, wherein said subject is a human.

20. The method of claim 1, wherein said composition is administered by one or more of the methods selected from the group consisting of intravenously, intraperitoneally, subcutaneously, intramuscularly, orally, topically and by aerosol.

21. The method of claim 20, wherein said composition is administered intraperitoneally, intramuscularly or subcutaneously in a range of about 0.01 to about 30 mg/kg or orally in a range of about 0.10 to about 50 mg/kg.

22. The method of claim 21, wherein said subject is a human.

* * * * *